(12) United States Patent
Brentano et al.

(10) Patent No.: US 6,245,519 B1
(45) Date of Patent: Jun. 12, 2001

(54) PROTECTION PROBES

(75) Inventors: Steven T. Brentano, Santee; Sherrol H. McDonough; Norman C. Nelson, both of San Diego, all of CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 09/502,966

(22) Filed: Feb. 11, 2000

Related U.S. Application Data

(60) Provisional application No. 60/120,019, filed on Feb. 12, 1999.

(51) Int. Cl.$^7$ ............................. C12Q 1/68; C07H 21/04
(52) U.S. Cl. ................................ 435/6; 536/24.3
(58) Field of Search ..................... 435/6, 91.2; 436/546; 536/24.3

(56) References Cited

U.S. PATENT DOCUMENTS

| | | | |
|---|---|---|---|
| 4,683,195 | 7/1987 | Mullis et al. | 435/6 |
| 4,766,064 | 8/1988 | Williams et al. | 435/6 |
| 4,950,613 | 8/1990 | Arnold, Jr. et al. | 436/546 |
| 5,283,174 | 2/1994 | Arnold, Jr. et al. | 435/6 |
| 5,348,853 * | 9/1994 | Wang et al. | 435/6 |
| 5,399,491 | 3/1995 | Kacian et al. | 435/91.21 |
| 5,639,604 | 6/1997 | Arnold, Jr. et al. | 435/6 |
| 5,731,148 | 3/1998 | Becker et al. | 435/6 |
| 5,824,475 * | 10/1998 | Nelson et al. | 435/6 |

FOREIGN PATENT DOCUMENTS

| | | |
|---|---|---|
| 0320308 | 11/1993 | (EP) . |
| 0639648 | 2/1995 | (EP) . |
| 0330433 | 4/1996 | (EP) . |
| 0709466 | 5/1996 | (EP) . |

OTHER PUBLICATIONS

Larry J. Kricka, Nonisotopic DNA Probe Techniques 275–310 ($1^{ST}$ ed. 1992).

Larry J. Kricka, Nonisotopic Probing, Blotting And Sequencing 391–428 ($2^{ND}$ ed. 1995).

Walker et al., "Strand displacement amplification—an isothermal, in vitro DNA amplification technique," *Nucleic Acids Research*, 20(7):1691–1696 (1992).

Cantor, "Lighting up hybridization", *Nature Biotechnology*, 14:247 (1996).

* cited by examiner

Primary Examiner—Kenneth R. Horlick
Assistant Examiner—Teresa Strzelecka
(74) Attorney, Agent, or Firm—Charles B. Cappellari; Sheldon O. Heber

(57) ABSTRACT

The present invention features compositions and methods that are useful for storing labeled detection probes and detecting whether a target nucleic acid sequence is present in a sample. Preferred compositions are made up of a detection probe containing a label susceptible to a chemical or enzymatic alteration and a protection probe that protects the label from alteration and/or decreases the ability of the detection probe to inhibit nucleic acid amplification. Such compositions can be used, for example, to stabilize a detection probe label and to prevent a detection probe from hybridizing prematurely to amplified or target nucleic acid.

62 Claims, 4 Drawing Sheets

SEQUENCE LISTING

```
<160> NUMBER OF SEQ ID NOS: 18

<210> SEQ ID NO: 1
<211> LENGTH: 23
<212> TYPE: RNA
<213> ORGANISM: Artificial Sequence
<220> FEATURE:
<223> OTHER INFORMATION: Description of Artificial Sequence: a
      synthetic detection probe with its terminal  3'OH blocked by
      an n-propyl group

<400> SEQUENCE: 1
ggaggauaug ucucagcgcu acc                                                 23

<210> SEQ ID NO: 2
<211> LENGTH: 23
<212> TYPE: DNA
<213> ORGANISM: Artificial Sequence
<220> FEATURE:
<223> OTHER INFORMATION: Description of Artificial Sequence: a
      synthetic detection probe with its terminal  3'OH blocked by
      an n-propyl group

<400> SEQUENCE: 2
ggaggatatg tctcagcgct acc                                                 23

<210> SEQ ID NO: 3
<211> LENGTH: 47
<212> TYPE: DNA
<213> ORGANISM: Artificial Sequence
<220> FEATURE:
<223> OTHER INFORMATION: Description of Artificial Sequence: a
      synthetic amplification primer

<400> SEQUENCE: 3
aatttaatac gactcactat agggagacca ggccacttcc gctaacc                       47

<210> SEQ ID NO: 4
<211> LENGTH: 24
<212> TYPE: DNA
<213> ORGANISM: Artificial Sequence
<220> FEATURE:
```

```
<223> OTHER INFORMATION: Description of Artificial Sequence: a
      synthetic amplification primer

<400> SEQUENCE: 4
cgcggaacag gctaaaccgc acgc                                              24

<210> SEQ ID NO: 5
<211> LENGTH: 38
<212> TYPE: DNA
<213> ORGANISM: Artificial Sequence
<220> FEATURE:
<223> OTHER INFORMATION: Description of Artificial Sequence: a
      synthetic helper probe

<400> SEQUENCE: 5
cggctgagag gcagtacaga aagtgtcgtg gttagcgg                               38

<210> SEQ ID NO: 6
<211> LENGTH: 36
<212> TYPE: DNA
<213> ORGANISM: Artificial Sequence
<220> FEATURE:
<223> OTHER INFORMATION: Description of Artificial Sequence: a
      synthetic helper probe

<400> SEQUENCE: 6
gggtaaccgg gtagggttg tgtgtgcggg gttgtg                                  36

<210> SEQ ID NO: 7
<211> LENGTH: 13
<212> TYPE: DNA
<213> ORGANISM: Artificial Sequence
<220> FEATURE:
<223> OTHER INFORMATION: Description of Artificial Sequence: a
      synthetic protection probe with its terminal 3'OH blocked by
      an n-propyl group

<400> SEQUENCE: 7
atgcgtcttg agg                                                          13

<210> SEQ ID NO: 8
<211> LENGTH: 11
<212> TYPE: DNA
<213> ORGANISM: Artificial Sequence
<220> FEATURE:
<223> OTHER INFORMATION: Description of Artificial Sequence: a
      synthetic protection probe with its terminal 3'OH blocked by
      an n-propyl group

<400> SEQUENCE: 8
tgcgtcttga g                                                            11

<210> SEQ ID NO: 9
<211> LENGTH: 19
<212> TYPE: RNA
<213> ORGANISM: Artificial Sequence
<220> FEATURE:
<223> OTHER INFORMATION: Description of Artificial Sequence: a
      synthetic detection probe

<400> SEQUENCE: 9
ggaccucaag acgcauguc                                                    19

<210> SEQ ID NO: 10
<211> LENGTH: 55
<212> TYPE: DNA
<213> ORGANISM: Artificial Sequence
```

```
<220> FEATURE:
<223> OTHER INFORMATION: Description of Artificial Sequence: a
      synthetic amplification primer

<400> SEQUENCE: 10
gaaattaata cgactcacta tagggagacc acagccgtca ccccaccaac aagct          55

<210> SEQ ID NO: 11
<211> LENGTH: 31
<212> TYPE: DNA
<213> ORGANISM: Artificial Sequence
<220> FEATURE:
<223> OTHER INFORMATION: Description of Artificial Sequence: a
      synthetic amplification primer

<400> SEQUENCE: 11
gggataagcc tgggaaactg ggtctaatac c                                    31

<210> SEQ ID NO: 12
<211> LENGTH: 24
<212> TYPE: DNA
<213> ORGANISM: Artificial Sequence
<220> FEATURE:
<223> OTHER INFORMATION: Description of Artificial Sequence: a
      synthetic detection probe

<400> SEQUENCE: 12
gtcttgtggt ggaaagcgct ttag                                            24

<210> SEQ ID NO: 13
<211> LENGTH: 47
<212> TYPE: DNA
<213> ORGANISM: Artificial Sequence
<220> FEATURE:
<223> OTHER INFORMATION: Description of Artificial Sequence: a
      synthetic target sequence

<400> SEQUENCE: 13
ctaaagcgct ttccaccaca agacatgcat cccgtggtcc tatccgg                   47

<210> SEQ ID NO: 14
<211> LENGTH: 17
<212> TYPE: DNA
<213> ORGANISM: Artificial Sequence
<220> FEATURE:
<223> OTHER INFORMATION: Description of Artificial Sequence: a
      synthetic protection probe with its terminal 3'OH blocked by
      an n-propyl group

<400> SEQUENCE: 14
gctttccacc acaagac                                                    17

<210> SEQ ID NO: 15
<211> LENGTH: 24
<212> TYPE: DNA
<213> ORGANISM: Artificial Sequence
<220> FEATURE:
<223> OTHER INFORMATION: Description of Artificial Sequence: a
      synthetic detection probe

<400> SEQUENCE: 15
agagtccgta gagcgatgag aacg                                            24

<210> SEQ ID NO: 16
<211> LENGTH: 15
<212> TYPE: DNA
<213> ORGANISM: Artificial Sequence
```

```
<220> FEATURE:
<223> OTHER INFORMATION: Description of Artificial Sequence: a
      synthetic protection probe

<400> SEQUENCE: 16
catcgctcta cggac                                                    15

<210> SEQ ID NO: 17
<211> LENGTH: 14
<212> TYPE: DNA
<213> ORGANISM: Artificial Sequence
<220> FEATURE:
<223> OTHER INFORMATION: Description of Artificial Sequence: a
      synthetic protection probe

<400> SEQUENCE: 17
cgctctacgg actc                                                     14

<210> SEQ ID NO: 18
<211> LENGTH: 24
<212> TYPE: DNA
<213> ORGANISM: Artificial Sequence
<220> FEATURE:
<223> OTHER INFORMATION: Description of Artificial Sequence: a
      synthetic target sequence

<400> SEQUENCE: 18
cgttctcatc gctctacgga ctct                                          24
```

PROTECTION PROBES

This application claims the benefit of U.S. Provisional Application No. 60/120,019, filed Feb. 12, 1999, the contents of which are hereby incorporated by reference herein.

FIELD OF INVENTION

The present invention relates to compositions for protecting detectable labels from chemical or enzymatic alteration and to their use in amplification and detection methods.

BACKGROUND OF THE INVENTION

None of the references described herein are admitted to be prior art to the claimed invention.

A target nucleic acid sequence can be detected by various methods using detection probes designed to preferentially hybridize to the target sequence over other sequences that may be present in a sample. Examples of target sequences include sequences initially present in a sample or produced as part of an amplification procedure.

Examples of detection probes include oligonucleotides and derivatives thereof able to preferentially hybridize to a target nucleic acid containing a target nucleic acid sequence over other nucleic acids that may be present in a sample. Hybridization of detection probes to target nucleic acid sequences results in the formation of detectable probe:target hybridization complexes under appropriate conditions.

Detecting detectable probe:target hybridization complexes is facilitated using a labeled detection probe. Different labels and assay formats can be used to detect the presence or amount of an analyte in a sample. Examples of detectable labels include radioisotopes, fluorescent molecules, chemiluminescent molecules, chromophors, enzymes, enzyme substrates and ligands. Examples of references describing the detection of nucleic acid using fluorescent and chemiluminescent molecules include Arnold et al., U.S. Pat. Nos. 5,283,174 and Becker et al. 5,731,148, both of which are hereby incorporated by reference herein.

To facilitate detection of a target nucleic acid sequence, the number of target sequences in a sample can be increased using nucleic acid amplification techniques. Nucleic acid amplification involves the enzymatic synthesis of nucleic acid containing a sequence complementary to a nucleic acid sequence being amplified. Nucleic acid amplification can be performed using different techniques such as those involving transcription-based amplification, the polymerase chain reaction (PCR), ligase chain reaction (LCR) and strand displacement amplification (SDA).

Transcription-based amplification of a nucleic acid sequence generally employs an RNA polymerase, a DNA polymerase, deoxyribonucleoside triphosphates, ribonucleoside triphosphates, and a promoter-template complementary oligonucleotide. The promoter-template complementary oligonucleotide contains a 5' sequence recognized by an RNA polymerase and a 3' sequence that hybridizes to a template nucleic acid in a location 3' of a sequence sought to be amplified. After hybridization of the promoter-template complementary oligonucleotide to the template, a double-stranded promoter is formed upstream from the target nucleic acid sequence. Double-stranded promoter formation generally involves DNA polymerase activity. Generally, a second oligonucleotide primer is employed to facilitate double-stranded promoter formation.

Transcription-based amplification involves the binding of an RNA polymerase to a promoter region that is usually double-stranded. The RNA polymerase proceeds downstream from the promoter region and synthesizes ribonucleic acid in a 5' to 3' direction. Multiple RNA transcripts are produced by transcription-based amplification using a single template.

Different formats can be employed for performing transcription-based amplification. Examples of different formats are provided in publications such as Burg et al., U.S. Pat. Nos. 5,437,990; Kacian et al., 5,399,491; Kacian et al., 5,554,516; McDonough et al., 5,766,849; Ryder et al., 5,786,183; Malek et al., 5,130,238; Kacian et al., International Application No. PCT/US93/04015, International Publication No. WO 93/22461; Gingeras et al., International Application No. PCT/US87/01966, International Publication No. WO 88/01302; Gingeras et al., International Application No. PCT/US88/02108, International Publication No. WO 88/10315; Davey and Malek, European Application No. 88113948.9, European Publication No. 0 329 822 A2; and Urdea, International Application No. PCT/US91/00213, International Publication No. WO 91/10746. (Each of these references is hereby incorporated by reference herein.)

PCR amplification is described by Mullis et al., U.S. Pat. Nos. 4,683,195, 4,683,202, and 4,800,159, and in *Methods in Enzymology*, 155:335–350 (1987). (Each of these references is hereby incorporated by reference herein.)

An example of LCR is described in European Patent Publication No. 320 308, which is hereby incorporated by reference herein. LCR uses at least four separate oligonucleotides. Two of the oligonucleotides hybridize to a nucleic acid template so that the 3' end of one oligonucleotide and the 5' end of the other oligonucleotide are positioned for ligation. The hybridized oligonucleotides are then ligated forming a full-length complement to the target nucleic acid sequence. The double-stranded nucleic acid is then denatured, and third and fourth oligonucleotides are hybridized to the complementary strand and joined together. Amplification is achieved by further cycles of hybridization, ligation, and denaturation, producing multiple copies of the target nucleic acid sequence and the sequence complementary to the target nucleic acid sequence.

SDA is an isothermal amplification reaction based on the ability of a restriction enzyme to nick the unmodified strand of a hemiphosphorothioate form of its recognition site, and on the ability of a DNA polymerase to initiate replication at the nick and displace a downstream non-template strand. (See, e.g., Walker, *PCR Methods and Applications*, 3:25–30 (1993), Walker et al., *Nucleic Acids Res.*, 20:1691–1996 (1992), and Walker et al., *Proc. Natl. Acad. Sci.* 89:392–396 (1991). (Each of these references is hereby incorporated by reference herein.) The steps used in generating fragments for carrying out autocatalytic SDA amplification are indicated to be adaptable for generating fragments for transcription-based amplification or amplification carried out using Q-beta technology (Walker et al., *Nucleic Acids Res.*, 20:1691–1696 (1992), which is hereby incorporated by reference herein.

SUMMARY OF INVENTION

The present invention features compositions and methods that are useful for storing labeled detection probes and detecting whether a target nucleic acid sequence is present in a sample. Preferred compositions are made up of a detection probe containing a label susceptible to a chemical or enzymatic alteration and a protection probe that protects the label from alteration and/or decreases the ability of the detection probe to inhibit nucleic acid amplification. Such compositions can be used, for example, to stabilize a detection probe label and to prevent a detection probe from hybridizing prematurely to amplified or target nucleic acid.

Chemical and enzymatic alterations of a detection probe label are changes in chemical identity or bonding effecting a signal produced from the altered label compared to a signal produced from an unaltered label. Examples of chemical and enzymatic alterations include oxidation, reduction, acid hydrolysis, base hydrolysis, alkylation and enzymatic cleavage or hydrolysis. Preferably, the chemical or enzymatic alteration causes a loss of signal detectability from the label.

A label susceptible to a chemical or enzymatic alteration, also referred to herein as a "susceptible label", contains a labile group that undergoes such alteration in an aqueous solution containing an agent normally able to act on the labile group. Preferably, a labile group is subject to hydrolysis in an aqueous solution having a pH between about pH 4 and about pH 9. Examples of labile groups include an ester linkage and a thioester linkage.

A protection probe protects the label from alteration when the label is altered to a lesser extent in the presence of the protection probe than in the absence of the protection probe. In preferred embodiments, the difference in alteration rates in the presence and the absence of the protection probe is at least about 10-fold, at least about 20-fold, and at least about 40-fold.

Detection and protection probes are molecules comprising nitrogenous bases that are purines, pyrimidines, or derivatives thereof. The nitrogenous bases are positioned on the probes so they can hydrogen bond with purine or pyrimidine bases present on a nucleic acid to form a hybridization complex. Such positioning also allows detection probe nitrogenous bases to hydrogen bond to protection probe nitrogenous bases to form a hybridization complex.

A detection probe can form a hybridization complex with a target nucleic acid sequence. The detection probe:target hybridization complex can be detected to indicate the presence of the target sequence. Preferred detection probes contain one or more detectable labels that can be used to facilitate determining whether detection probe:target hybridization complexes are present.

A protection probe can be used to protect a detection probe label susceptible to a chemical or enzymatic alteration from such alteration by forming a detection probe:protection probe hybridization complex. The protection probe can be removed from the detection probe at a later time allowing the detection probe to be used to detect the presence of a target sequence.

A detection probe:protection probe hybridization complex can also be used to reduce hybridization of the detection probe to amplified nucleic acids during amplification. Increasing the number of target nucleic acid sequences using nucleic acid amplification techniques can facilitate detection of a target nucleic acid sequence. However, detection probes present during nucleic acid amplification can inhibit amplification by hybridizing to amplification products before amplification is finished.

Detection probes present in detection probe:protection probe hybridization complexes are not free to hybridize to amplified nucleic acid. After amplification, the stringency conditions can be raised to destabilize detection probe:protection probe hybridization complexes while allowing for the formation of detection probe:target hybridization complexes. Additionally, the presence of excess target nucleic acid produced by the amplification helps drive the formation of detection probe:target hybridization complexes.

Thus, a first aspect of the present invention describes a composition comprising (1) a detection probe comprising a label susceptible to a chemical or enzymatic alteration, and (2) a protection probe that protects the label from such alteration. The hybridization complex formed between the detection probe and the protection probe has a lower Tm than a hybridization complex formed between the detection probe and a fully complementary target nucleic acid.

"Hybridized" and "hybridization complex" refer to stable hybridization complexes. Stable hybridization complexes have a Tm at, or higher, than the solution temperature.

Preferably, the protection probe does not form a "hydrolysis protecting adduct" with the label. A "hydrolysis protecting adduct" refers to an adduct formed between a protective adduct forming molecule and a susceptible label that protects the label from hydrolysis.

Reference to a "fully complementary target nucleic acid" of the detection probe indicates that either, or both, the DNA complement or RNA complement can be used as a reference oligonucleotide to determine whether the detection probe has the described property. The DNA complement is a deoxyribonucleic acid of the same length as the detection probe where each nucleotide present can hydrogen bond to the detection probe by Watson-Crick (e.g., A-T, G-C) hydrogen bonding. The RNA complement is a ribonucleic acid of the same length as the detection probe where each nucleotide present can hydrogen bond to the detection probe by Watson-Crick hydrogen bonding.

Preferably, the composition further comprises an aqueous solution able to chemically or enzymatically alter a susceptible label, and the protection probe protects the label from alteration. More preferably, the susceptible label can be hydrolyzed in the aqueous solution, and the protection probe protects the label from hydrolysis.

In preferred embodiments, the susceptible label is a chemiluminescent label; the susceptible label is an optionally substituted acridinium ester; and chemiluminescence from the susceptible label proceeds via an electronically excited optionally substituted N-alkyl acridone.

In additional preferred embodiments the protection probe and the detection probe are present in an aqueous solution not containing target nucleic acid, and the composition "consists essentially of" or "consists of" the protection probe, the detection probe and the aqueous solution. "Consisting essentially of" when used as a claim transition phrase limits the scope of a claim to (1) specified materials or steps and (2) to materials or steps not materially affecting the basic characteristic(s) of the claimed invention.

Another aspect of the present invention describes a composition comprising (1) an aqueous solution, (2) a detection probe comprising a label susceptible to a chemical or enzymatic alteration in the aqueous solution, and (3) a protection probe that protects the label from alteration. The detection probe and the protection probe are stored in the aqueous solution for at least 1 day (i.e., 24 hours). Preferably, the protection probe does not form a "hydrolysis protecting adduct" with the label.

Another aspect of the present invention describes a composition comprising (1) an aqueous solution, (2) a detection means for detecting the presence of a nucleic acid sequence, wherein the detection means comprises a label susceptible to a chemical or enzymatic alteration in the aqueous solution, and (3) a label protection means for inhibiting the alteration of the label. A hybridization complex formed between the detection means and the label protection means has a lower Tm in the aqueous solution than a hybridization complex formed between the detection means and a fully complementary target nucleic acid. Preferably, the label protection means does not form a hydrolysis protecting adduct with the label.

"Detection means" refers to material described in the present application and equivalents thereof for detecting the presence of a nucleic acid target sequence. "Label protection means" refers to material described in the present application and equivalents thereof for inhibiting the chemical or enzymatic alteration of a detection probe label.

Another aspect of the present invention describes a composition comprising (1) an aqueous solution, (2) a detection means for detecting the presence of a nucleic acid sequence, wherein the detection means comprises a label susceptible to a chemical or enzymatic alteration in the aqueous solution; and (3) a label protection means for inhibiting alteration of the label, provided that the detection means and the label protection means are stored together for at least 1 day. Preferably, the label protection means does not form a hydrolysis protecting adduct with the label.

Another aspect of the present invention describes a composition consisting essentially of (1) a detection means for detecting the presence of a target nucleic acid sequence, (2) an inhibiting means for inhibiting the ability of the detection means to hybridize to the target sequence during an isothermal amplification reaction, and (3) an optionally present aqueous solution. A hybridization complex formed between the detection means and the inhibiting means has a lower Tm than a hybridization complex formed between the detection means and a fully complementary target nucleic acid of the detection means. Preferably, the inhibiting means does not form a hydrolysis protecting adduct with the detection means.

"Inhibiting means" refers to material described in the present application and equivalents thereof for inhibiting the ability of the detection means to hybridize to the target nucleic acid sequence during an isothermal amplification reaction.

Isothermal amplification occurs under conditions of essentially constant temperature where the temperature is not alternately raised and lowered to achieve melting then annealing of nucleic acid, such as that occurring in PCR. In one embodiment, the temperature does not change more than about 5° C. Preferably, isothermal amplification is performed under conditions where the temperature is not changed by any external forces, such as by heating or cooling.

Another aspect of the present invention describes a method of determining whether a target nucleic acid sequence is present in a sample involving the production of amplified target nucleic acid sequences. The method comprises the steps of:

a) producing a reaction mixture comprising the sample and a composition comprising a detection probe hybridized to a protection probe, b) exposing the reaction mixture to amplifying conditions such that the target sequence, if present, is used to produce amplified nucleic acid, and c) detecting whether the detection probe is hybridized to the amplified nucleic acid under detection conditions as an indication that the target nucleic acid sequence is present in the sample.

Under amplifying conditions the detection probe is hybridized to the protection probe. Under detection conditions the detection probe is not stably hybridized with the protection probe, but can hybridize to the amplified nucleic acid if present. By "not stably hybridized" is meant that the hybridization complex, if present, has a Tm less than the temperature of the solution.

In a preferred embodiment the detection probe comprises a susceptible label and the protection probe protects the label from chemical or enzymatic alteration in the reaction mixture or under amplifying conditions. More preferably, the protection probe does not form a hydrolysis protecting adduct with the label.

Another aspect of the present invention describes a method of determining whether a target nucleic acid sequence is present in a sample comprising the steps of:

a) producing a reaction mixture comprising a detection probe hybridized to a protection probe, where the detection probe comprises a label susceptible to a chemical or enzymatic alteration and the protection probe protects the label from alteration, and b) providing the reaction mixture to the sample and detecting whether the detection probe is hybridized to the target sequence under detection conditions as an indication that the target sequence is present in the sample. Preferably, the protection probe does not form a hydrolysis protecting adduct with the label.

Various examples are described herein. These examples are not intended in any way to limit the claimed invention. Thus, unless otherwise stated in a claim, reference to one or more example(s) in the specification does not limit the claimed invention to the indicated example(s).

Other features and advantages of the invention will be apparent from the following drawings, the description of the invention, the examples, and the claims.

DETAILED DESCRIPTION OF THE INVENTION

Figure 1:
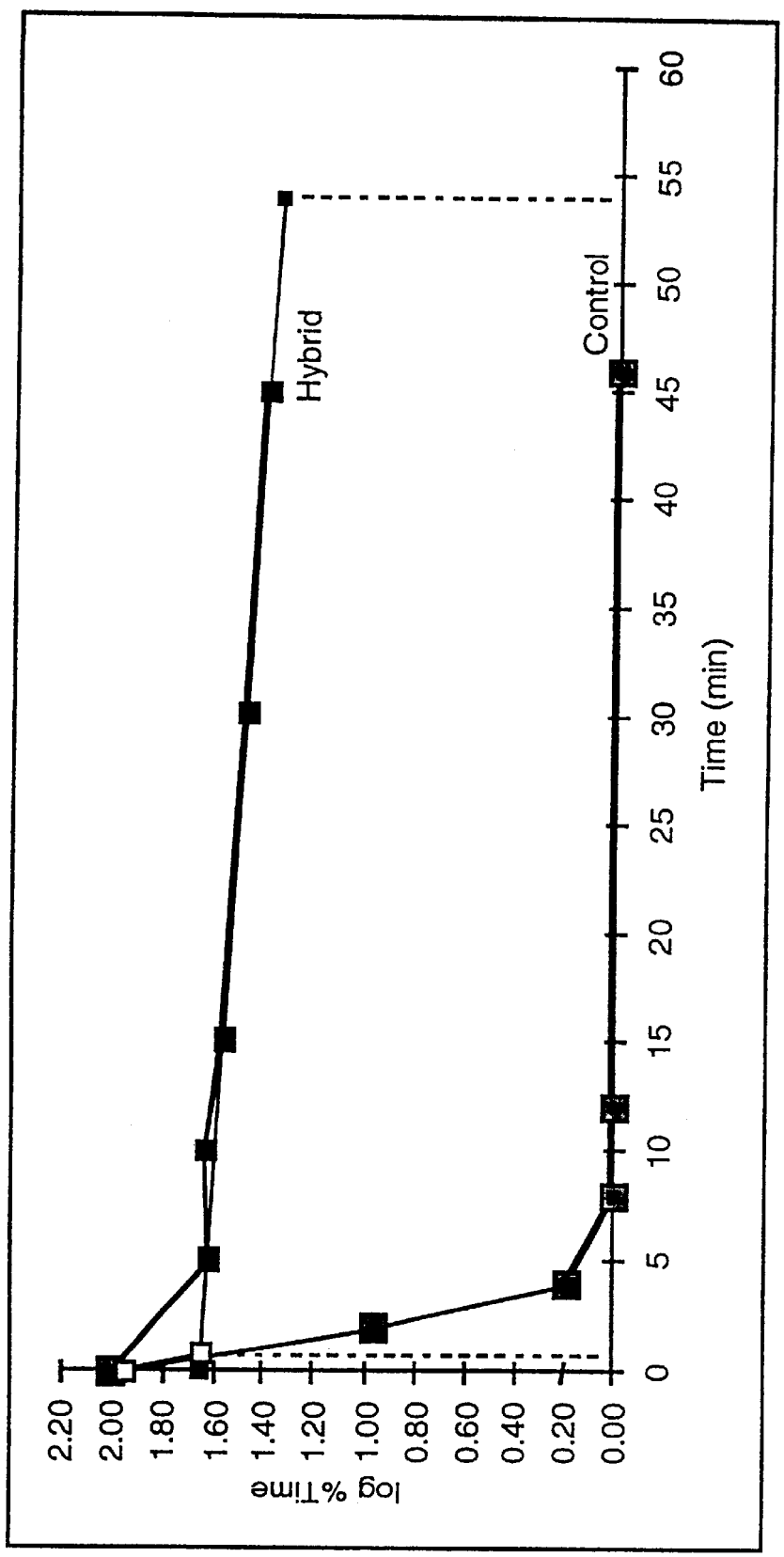
FIG. 1 illustrates a loss of detectable signal with time using AE-labeled probe SEQ. ID. No. 12 with excess protection probe SEQ. ID. No. 14 as target. The log of the percent input RLU was plotted versus time.

The present invention features compositions and methods useful for storing detection probes and detecting the presence of a target nucleic acid sequence in a sample. Preferred compositions contain a protection probe that protects a label susceptible to chemical or enzymatic alteration from such alteration and/or decreases the ability of the detection probe to inhibit nucleic acid amplification.

Label Protecting Hybridization Complexes

Based on the guidance provided herein, detection probe:protection probe hybridization complexes can be produced to protect one or more susceptible labels present on a detection probe from alteration in an aqueous solution containing an agent able to chemically or enzymatically alter the label. Protection of a susceptible label from alteration is achieved by a protective hybridization microenvironment produced by a detection probe:protection probe hybridization complex.

Preferably, a susceptible label is positioned internally within a detection probe:protection probe hybridization complex between groups, such as nucleotide bases, involved in hydrogen bonding. In different embodiments the detection probe:protection probe hybridization complex contains at least 3, at least 5, or at least 7, groups involved in hydrogen bonding on each side of any susceptible label which is present in the hybridization complex.

Factors concerning the stability of labels in a probe:target hybridization complex are discussed in different references such as Arnold et al., U.S. Pat. No. 5,639,604, and Nelson et al., "Detection Of Acridinium Esters By Chemiluminescence" In: Nonisotopic DNA Probe Techniques, (Kricka ed., Academic Press, 1992) pp. 275–311 (both of which are hereby incorporated by reference herein). Based on the disclosure provided herein, such factors can be applied to label protection in a detection probe:protection probe hybridization complex.

The protection probe can protect a label from chemical or enzymatic alteration without forming a hydrolysis protecting adduct with the label. The use of adduct formation to protect a label from alteration prior to a detection method is described by Arnold et al. U.S. Pat. No. 4,950,613, which reference is hereby incorporated by reference herein. Advantages of forming a hybridization complex to protect the detection probe label, rather than forming a protective adduct using an adduct former, include the ease with which the detection probe label can be removed from the protecting group (the protection probe) to facilitate the use of the detection probe to detect the presence of a target nucleic acid.

Amplification

The present invention can be used to provide a detection probe, hybridized to a protection probe, to a sample prior to an amplification. The ability of the detection probe to interfere with an amplification is inhibited when it is hybridized to the protection probe.

Preferably, this aspect of the invention employs an isothermal amplification. More preferably, the isothermal amplification is performed at a temperature below the detection probe:protection probe Tm. Isothermal amplification techniques are well known in the art, and examples are provided in the "BACKGROUND OF THE INVENTION" supra. More preferably, detection probe:protection probe hybridization complexes are used in conjunction with transcription-based amplification.

More preferably, the detection probe present in a detection probe:protection probe hybridization complex contains a label that is protected by the hybridization complex from chemical or enzymatic alteration.

Providing the detection probe to a sample prior to an amplification simplifies a detection method by reducing the number of steps where a reagent needs to be added. However, the presence of a detection probe available for hybridization to amplified nucleic acid can inhibit further amplification of the amplified nucleic acid. Detection probes present in detection probe:protection probe hybridization complexes are not available to hybridize to amplified nucleic acid.

After amplification, the stringency of the environment containing amplified nucleic acid can be raised to separate the detection probe from the detection probe:protection probe hybridization complex. For example, heat can be applied to destabilize detection probe:protection probe hybridization complexes while providing an environment suitable for stable detection probe:target hybridization complexes. Additionally, the increased number of target nucleic acids produced by the amplification helps drive the formation of detection probe:target hybridization complexes.

The detection probe:protection probe hybridization complex Tm is preferably at least about 2° C. greater than the temperature used during amplification conditions. In different embodiments the detection probe:protection probe hybridization complex Tm is at least about 5° C., or at least about 10° C. greater than the temperature used during amplification conditions.

Target Sequence Bias

The detection probe can be biased towards the target nucleic acid sequence to form a more stable hybridization complex with the target sequence than with the protection probe using different design considerations affecting hybridization complex stability. Such considerations include the degree of complementarity, the type of complementary recognition groups, and the backbone structure. The effects of these considerations vary depending upon the environmental conditions.

The degree of complementarity takes into account the number of groups present on the detection probe that hydrogen bond with groups present on the protection probe and on the target nucleic acid. The detection probe can be designed to have a greater degree of complementarity to the target nucleic acid than to the protection probe using different techniques. Such techniques include, for example, designing the detection probe to have mismatches with the protection probe, but not with the target nucleic acid, and the use of non-nucleotide linkers. In different embodiments, the protection probe is shorter than the detection probe, and the protection probe is not perfectly complementary to the detection probe.

Examples of non-nucleotide linkers include polysaccharides, peptides, polypeptides, and sugar phosphate nucleotide backbones lacking a nucleotide nitrogenous base able to hydrogen bond to a nucleic acid. Additional examples are provided by Arnold et al. International Application No. PCT/US88/03 173, International Publication WO 89/02439, and U.S. Pat. No. 5,585,481, both of which are hereby incorporated by reference herein.

The types of groups present in a detection probe and a protection probe can be chosen to bias the detection probe towards the target nucleic acid sequence by also taking into account factors such as the degree of hydrogen bonding between different nitrogenous bases. For example, G-C pairing or 2,6 diaminopurine-thymine pairing is stronger than A-T pairing and pairing with universal bases such as inosine. The detection probe can be designed to have increased G or C pairing with nucleotides present in a target nucleic acid sequence compared to the protection probe.

The composition of protection and detection probe backbones can be adjusted in different ways to bias the detection probe towards a target nucleic acid sequence. Examples of such backbones include sugar-phosphodiester type linkages, such as those present in ribo- and deoxyribonucleic acids, or derivative thereof; and a peptide linkage, such as that present in peptide nucleic acid.

Peptide nucleic acid may form a more stable hybridization complex with RNA than with the corresponding DNA sequence. Thus, the detection probe can be biased towards an RNA target nucleic acid sequence, for example, by using a detection probe containing peptide nucleic acid groups and a protection probe made up of DNA.

In the case of a sugar-phosphodiester type linkage, both the sugar groups and the linkage joining two sugar groups will affect hybridization complex stability. An example of the affect the sugar can have is that seen with 2'-methoxy substituted RNA. 2'-Methoxy containing nucleic acids generally form more stable hybridization complexes with RNA than with the corresponding DNA sequence. Another example, is 2'-fluoro substituted RNA which has the same type of affect as 2'-methoxy substituted RNA.

Examples of ways in which the backbone may affect hybridization complex stability include affecting the charge density and the physical association between two strands. Steric interactions from bulky groups can reduce hybridization complex stability. Groups such as phosphorothioates can reduce hybridization complex stability, whereas uncharged groups such as methylphosphonates can increase hybridization complex stability.

Detection Conditions

Detection conditions are used to destabilize protection probe:detection probe hybridization complexes and provide an environment allowing for the formation of detection probe:target hybridization complexes. The selection of appropriate detection conditions takes into account factors such as the detection probe:protection probe hybridization complex Tm, detection probe:target hybridization complex Tm, and the difference between the Tm of the such hybridization complexes.

Depending upon the composition of an assay, the Tm of a hybridization complex will vary. Assay factors such as salt concentration and the presence of denaturing agents affect the Tm of a given hybridization complex. Such factors are well known in the art.

The detection probe:target hybridization complex Tm is preferably at least about 3° C. greater than the temperature used during detection conditions. In different embodiments the detection probe:target hybridization complex Tm is at least about 5° C., or at least about 10° C., greater than the temperature used during detection conditions.

The detection probe:protection probe hybridization complex Tm is preferably at least about 2° C. lower than the temperature used during detection conditions. In different embodiments the detection probe:protection probe hybridization complex Tm is at least about 5° C., or at least about 10° C., lower than the temperature used during detection conditions.

Preferably, the detection probe:target hybridization complex Tm is at least about 5° C. greater than the detection probe:protection probe hybridization complex Tm. In different embodiments the detection probe:target hybridization complex Tm is at least about 8° C., at least about 10° C., or at least about 15° C., greater then the detection probe:protection probe hybridization complex Tm.

Determining whether a label is present is performed using techniques compatible with detectable labels that are present and may involve changing the detection conditions. Examples of techniques for determining whether detectable labels, such as, acridinium esters, are provided by Arnold et al. U.S. Pat. No. 5,639,604, and Becker et al. U.S. Pat. No. 5,731,148, both of which are hereby incorporated by reference herein. Additional techniques that can be used to detect different types of labels are well known in the art.

Storage and Stability

Protection probes can be used to stabilize detection probe labels susceptible to a chemical or enzymatic alteration facilitating the storage of labeled detection probes. Efficient hybridization of the protection probe to the detection probe during storage can be achieved using appropriate conditions and probe concentrations.

Preferably, the protection probe is used in an excess amount to the detection probe. In different embodiments, the protection probe is present in at least about 2-fold, at least about 10-fold, at least about 20-fold, at least about 50-fold, or at least about 100-fold, excess to the detection probe.

Preferably, storage is carried out in a solution at a temperature at least about 10° C., or at least about 20° C., lower than the protection probe:detection probe Tm.

Additional considerations for achieving efficient hybridization of the protection probe to the detection probe include pH, the presence of a buffer, salt concentration, and temperature. An example of storage conditions for acridinium ester labels is 2× Hybridization Buffer (see Example section infra) buffered to a pH of about 5.1 and a temperature of about 4° C. Based on the present application other suitable storage conditions for acridinium esters and other types of labels can readily be obtained.

In one embodiment, storage conditions employ a temperature between about 4° C. and about 42° C. Generally, a lower temperature is useful for increasing detection probe label stability. A disadvantage of employing lower temperatures is the need for refrigeration. Protection probes can be used to stabilize detection probe labels without employing lower temperatures, and can be used to stabilize the detection probe label at room temperature. In different embodiments the protection and detection probes are stored in an environment having a temperature range of about 16° C. to about 30° C., about 16° C. to about 25° C., about 18° C. to about 30° C., and about 18° C. to about 25° C.

The protection probe can be used to increase the time in which a detection probe label can be stored for future use. In different embodiments the protection and detection probe are stored together for at least about 1 day, at least about 2 days, at least about 2 weeks, at least about two months, and at least about 6 months. In additional embodiments, the protection and detection probe are stored no more than 6 months, no more than 4 months, no more than 2 months, no more than one month, and no more than 2 weeks.

Probe Construction

Protection and detection probes comprise nucleic acid binding regions made up of nucleotide base recognition groups joined together by a backbone. The nucleotide base recognition groups are positioned so that they can hydrogen bond to nucleotides present in a nucleic acid.

Protection and detection probes may also contain groups not part of a nucleic acid binding region. Examples of such groups are nucleotides, or other types of groups, positioned on the ends of the protection and detection probe which do not participate in a detection probe:protection probe hybridization complex or a detection probe:target hybridization complex.

A given nucleotide base recognition group present in a detection or protection probe may be complementary to a particular nucleotide (e.g., adenine, guanine, cytosine, thymine, and uracil), and thus, be able to hydrogen bond with that nucleotide. A nucleotide base recognition group may also be able to hydrogen bond with different nucleotides. For example, when inosine is a nucleotide base recognition group it can hydrogen bond with different nucleotide bases.

Preferred nucleotide base recognition groups are nitrogenous purine or pyrimidine bases, or derivatives thereof, able to hydrogen bond with adenine, guanine, cytosine, thymine or uracil. Examples of such recognition groups include adenine, guanine, cytosine, thymine, uracil, and derivatives thereof. Examples of derivatives include modified purine or pyrimidine bases such as $N^4$-methyl deoxyguanosine, deaza or aza purines and pyrimidines used in place of natural purine and pyrimidine bases, pyrimidine bases having substituent groups at the 5 or 6 position, and purine bases having an altered or a replacement substituent at the 2, 6 or 8 positions. See, e.g., Cook, International Application No. PCT/US92/11339, International Publication No. WO 93/13121 (hereby incorporated by reference herein). Additional examples include, 2-amino-6-methylaminopurine, O6-methylguanine, 4-thio-pyrimidines, 4-amino-pyrimidines, 4 -dimethylhydrazine-pyrimidines, O4-alkyl-pyrimidines (see, e.g., *The Glen Report, Volume* 1 (1993), hereby incorporated by reference herein).

Protection and detection probe backbones can each be made up of the same, or different, groups. Examples of backbone groups include sugar-phosphodiester type backbone groups and peptide nucleic acid backbone groups.

Structure I illustrates a sugar-phosphodiester type backbone where the sugar group is a pentofuranosyl group. The sugar groups are joined together by a linkage such as a phosphodiester linkage or other suitable linkage.

Structure I

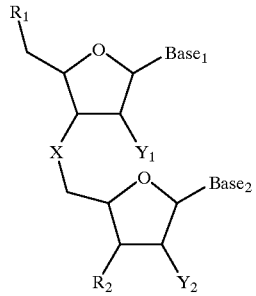

X represents the group joining two sugars. Examples of X include —OP(O)$_2$O—, —NHP(O)$_2$O—, —OC(O)$_2$O—, —OCH$_2$C(O)$_2$NH—, —OCH$_2$C(O)$_2$O—, —OP(CH$_3$)(O)O—, —OP(S)(O)O— and —OC(O)$_2$NH—. As with the other examples provided herein, other equivalents that are well known in the art or which become available can also be used.

$Y_1$ and $Y_2$ are independently selected groups. Examples of $Y_1$ and $Y_2$ include H, OH, $C_1$–$C_4$ alkoxy, halogen, and $C_1$–$C_6$ alkyl. Preferably, $Y_1$ and $Y_2$ are independently either H, OH, F, or OCH$_3$. $C_1$–$C_6$ alkyl and $C_1$–$C_4$ alkoxy, may include groups which are straight-chain, branched, or cyclic.

Base$_1$ and Base$_2$ are nucleotide base recognition groups able to hydrogen bond to adenine, guanine, cytosine, thymine, uracil, or a group that does not prevent complementary base pairing of an adjacent base to a complementary nucleic acid. Preferably Base$_1$ and Base$_2$ are independently selected from the group consisting of: adenine, guanine, cytosine, thymine, or uracil, or a group that does not prevent complementary base pairing of an adjacent base to a complementary nucleic acid. Examples of groups not preventing complementary base pairing include smaller size groups such as hydrogen, OH, $C_1$–$C_6$ alkyl, and $C_1$–$C_4$ alkoxy.

$R_1$ and $R_2$ represent independently selected groups. Examples of $R_1$ and $R_2$ include additional sugar-phosphodiester type groups, hydrogen, hydroxy, peptide nucleic acid, phosphate, thiophosphate, $C_1$–$C_6$ alkyl, an inverted (3'—3') nucleotide, 3'-deoxynucleotide, polysaccharides, polypeptides, peptides, and non-nucleotide linkers such as those described in Arnold et al. U.S. Pat. No. 5,696,251.

A derivative of the Structure I molecule can also used as a component of a detection or protection probe. For example, detection and protection probes can have cyclobutyl moieties connected by linking moieties, where the cyclobutyl moieties have heterocyclic bases attached thereto. See, e.g., Cook et al., International Application No. PCT/US93/01579, International Publication No. WO 94/19023 (hereby incorporated by reference herein).

In an embodiment of the present invention, the protection and detection probes are each a polynucleotide or derivative thereof. A "polynucleotide or derivative thereof" is made up of Structure I repeating units where X is —OP(O)$_2$O—; $Y_1$ and $Y_2$ are independently selected from the group consisting of H, OH, OCH$_3$, and F; Base$_1$ and Base$_2$ are independently selected from the group consisting of: adenine, guanine, cytosine, thymine, and uracil; and the terminal portion of the molecule contains $R_1$ and $R_2$ independently selected from the group consisting of OH, $C_1$–$C_6$ alkyl, phosphate, thiophosphate, an inverted nucleotide, and a 3' deoxynucleoside.

Another type of backbone is that present in peptide nucleic acid. Peptide nucleic acid is a DNA analogue where the deoxyribose phosphate backbone is replaced by a pseudo peptide backbone. Peptide nucleic acid is described by Hyrup and Nielsen, *Bioorganic & Medicinal Chemistry*, 4:5–23 (1996), and Hydig-Hielsen and Godskesen, International Application No. PCT/DK95/00195, International Publication No. WO 95/32305, each of which is hereby incorporated by reference herein.

An example of peptide nucleic acid, made up of N-(2-aminoethyl)glycine units, is illustrated in Structure II.

Structure II

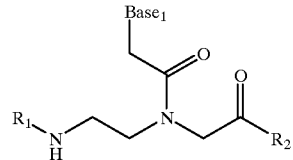

$R_1$, $R_2$, and Base$_1$ is as described for Structure I type molecules.

Protection and detection probes can be produced using standard techniques. Publications describing organic synthesis of oligonucleotides and modified oligonucleotides include Eckstein, F., *Oligonucleotides and Analogues, A Practical Approach*, Chapters 1–5 (1991), which reviews organic synthesis of oligonucleotides; Caruthers et al., *In Methods In Enzymology* 154:287 (1987), which describes a procedure for organic synthesis of oligonucleotides using standard phosphoramidite solid-phase chemistry; Bhatt, U.S. Pat. No. 5,252,723, which describes a procedure for organic synthesis of modified oligonucleotides containing phosphorothioate linkages; and Klem et al., International Application No. PCT/US91/07630, International Publication No. WO 92/07864, which describes organic synthesis of modified oligonucleotides having different internucleotide linkages including methylphosphonate linkages. (Each of these references is hereby incorporated by reference herein.)

Additional references describing techniques which can be used to produce different types of protection and detection probes include Cook, International Application No. PCT/US92/11339, International Publication No. WO 93/13121; Miller et al., International Application No. PCT/US94/00157, International Publication No. WO 94/15619; McGee et al., International Application No. PCT/US93/06807, International Publication No. WO 94/02051; Cook et al., International Application No. PCT/US93/01579, International Publication No. WO 94/19023; Hyrup and Nielsen, Bioorganic & Medicinal Chemistry, 4:5–23 (1996); and Hydig-Hielsen and Godskesen, International Application No. PCT/DK95/00195, International Publication No. WO 95/32305. (Each of these references is hereby incorporated by reference herein.)

In an embodiment of the present invention, the protection probe and the detection probe are each made up of optionally modified oligonucleotides. Optionally modified oligonucleotides may contain peptide nucleic acid, altered sugar groups, altered phosphodiester linkages, and/or altered nitrogenous bases. Preferred modifications include different purine or pyrimidine nitrogenous bases, or derivatives thereof, able to hydrogen bond to adenine, guanine, thymine or cytosine; different sugar moieties such as 2' alkoxy ribose, 2' halo ribose and cyclobutyl; different internucleotide linkages such as methylphosphonate and phosphorothioate; and a blocking group. Preferably, the 2' alkoxy ribose, if present, is 2' methoxy ribose, and the 2' halo ribose, if present, is 2' flouro ribose.

More preferably, the protection probe and the detection probe are each optionally modified oligonucleotides comprising one or more modifications independently selected from the group consisting of: 2'-methoxy ribose, 2'-halo ribose, methylphosphonate linkage, phosphorothioate linkage, and a 3' blocking group.

Protection and detection probes present during an amplification are preferably modified with a polymerase blocking group. Blocking groups are typically located at the terminal 3' end of a probe that is made up of nucleotides or derivatives thereof containing a 3' OH prior to the addition or formation of the blocking group. By attaching a blocking group to a terminal 3' OH, the 3' OH group is no longer available to accept a nucleoside triphosphate in a polymerization reaction. A blocking group can be formed, for example, by removing the 3' OH from a terminal nucleotide.

Numerous different groups can be added to block the 3' end of a probe from being used in a polymerization reaction. Examples of such groups include an alkyl group, a non-nucleotide linker, phosphorothioate, alkane-diol residue, a peptide nucleic acid, 3' deoxynucleoside (e.g., cordycepin), and an inverted nucleotide.

An alkyl blocking group is a saturated hydrocarbon up to 12 carbons in length that can be straight chain, branched, and/or cyclic. More preferably, the alkyl blocking group is a $C_2$–$C_6$ alkyl that can be straight chain, branched, and/or cyclic.

In different embodiments concerning the overall length of the protection and detection probes, the probes are preferably about 8 to about 40, about 8 to about 35, about 8 to about 25, or about 8 to about 20, nucleotides and/or optionally modified nucleotides in length.

Detectable Labels

Numerous different labels can be used to detect the presence of a target nucleic acid sequence. Examples of such labels include luminescent molecules, enzymes, cofactors, enzyme substrates, and haptens or other ligands.

Appropriate labels should be chosen which do not prevent the detection probe from specifically hybridizing to the target nucleic acid sequence. Thus, the label should not prevent the detection probe from distinguishing between the target sequence and other nucleic acids present in the sample.

Preferred labels for use with the present invention are luminescent labels such as fluorescent or chemiluminescent labels. More preferably, chemiluminescent labels are used.

A chemiluminescent label can be triggered to emit light by a chemical reaction such as heating and oxidation, while fluorescent label emission can be triggered by light. Labels that can be caused to emit light by a chemical reaction are generally able to fluoresce, though in some cases triggering of a "chemiluminescent" label by light may result in lesser light emission than chemiluminescence. Thus, chemiluminescent labels are generally also fluorescent labels. Examples of luminescent labels and their use are described by Arnold et al. U.S. Pat. No. 5,639,604, and Becker et al. U.S. Pat. No. 5,731,148 (both of which are hereby incorporated by reference herein).

Chemiluminescent labels are chemically induced to emit light by a triggering agent causing the formation of an excited state molecule that decays, thereby emitting light. To facilitate light emission, the chemiluminescent label may contain a leaving group joined to a light emitting molecule through a labile group that is cleaved during the chemical reaction causing light emission. Examples of such labile groups include an ester linkage and a thioester linkage.

Examples of chemiluminescent labels, the production of such labels, the joining of the labels to a detection probe, and factors generally affecting chemiluminescent label stability are well known in the art. These factors include the structure of the chemiluminescent molecule, the type and position of substituents on the chemiluminescent portion of the molecule and on a leaving group, and the structure of the linking group joining a leaving group to the light emitting portion of the molecule. See, Beheshti et al., U.S. Pat. Nos. 5,290,936; Campbell et al., 4,946,958; Law et al., 4,918,192, 4,745,181, 5,110,932 and 5,241,070; McCapra et al., 5,281,712; and McCapra et al., European Patent Application No. 88121915.8, European Patent Publication No. 0 322 926. (Each of these references is hereby incorporated by reference herein.)

Preferred chemiluminescent molecules are those having a labile group that can be protected by the protection probe from a chemical or enzymatic alteration affecting label detectability and which have the following structure:

Structure III

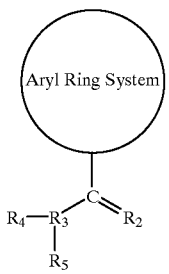

where the aryl ring system comprises one to four cyclic groups, and one of the groups is joined to linking carbon "c", more preferably the aryl ring system is positively charged, more preferably the aryl ring system contains a positively charged heterocyclic aryl joined to "c"; examples of heterocyclic aryls include acridinium, benz[a]acridinium, benz[b]acridinium, benz[c]acridinium, a benzimidazole cation, quinolinium, isoquinolinium, quinolizinium, cyclic substituted quinolinium, pyridinium, pyrimidininium, pyridazinium, pyrazininium, phenathridinium and quinozalinium;

$R_2$ is selected from the group consisting of S, O, and NH, preferably $R_2$ is O;

$R_3$ is selected from the group consisting of O, N, S, halogen, substituted phosphorous, substituted sulfur, preferably $R_3$ is either O, N, or S, more preferably $R_3$ is O or S, most preferably $R_3$ is O;

$R_4$ is selected from the group consisting of alkyl, alkenyl, aryl, or is absent when $R_3$ is halogen, preferably $R_4$ is an aryl, more preferably $R_4$ is an optionally substituted phenyl; and $R_5$ is nothing unless $R_3$ is N; if $R_3$ is N then $R_5$ is selected from the group consisting of hydrogen, alkyl, alkenyl, and aryl. Preferably $R_5$ is nothing.

Generally, the label will be joined to the detection probe through a linker attached to $R_4$. However, the label can be attached to the detection probe through a linker attached to a group other than $R_4$.

Positively charged Structure III molecules are ionically associated with a counter-ion. Various different anions such as a halogen, sulfate, alkylsulfate, halosulfate, haloborate, haloacetate, halophosphate, and phosphate can serve as a counter-ion.

An "acetyl" refers to $C(=O)-CH_3$.

An "alkenyl" refers to an optionally substituted hydrocarbon containing at least one double bond, including straight-chain, branched-chain, and cyclic alkenyl groups. Preferably, the alkenyl has 2 to 10 carbons and contains no more than 1 heteroatom. Heteroatoms are preferably selected from the group consisting of nitrogen, sulfur, phosphorus, and oxygen. More preferably, it is a lower alkenyl of from 2 to 6 carbons, more preferably 2 to 4 carbons.

An "alkyl" refers to an optionally substituted saturated aliphatic hydrocarbon, including straight-chain, branched-chain, and cyclic alkyl groups. Preferably, the alkyl has 1 to 10 carbons and contains no more than 1 heteroatom. Heteroatoms are preferably selected from the group consisting of nitrogen, sulfur, phosphorus, and oxygen. More preferably, it is a lower alkyl of from 1 to 6 carbons, more preferably 1 to 4 carbons.

An "alkoxy" refers to "—O-alkyl" where "alkyl" is defined as described above and "O" is an oxygen. Preferably, the alkoxy is a O-lower alkyl.

An "alkynyl" refers to an optionally substituted unsaturated hydrocarbon containing at least one triple bond, including straight-chain, branched-chain, and cyclic alkynyl groups. Preferably, the alkynyl has 2 to 10 carbons and contains no more than 1 heteroatom. Heteroatoms are preferably selected from the group consisting of nitrogen, sulfur, phosphorus, and oxygen. More preferably, it is a lower alkynyl of from 2 to 6 carbons, more preferably 2 to 4 carbons.

An "amido" refers to $C(=O)-NH_2$.

An "amino" refers to $-NH_2$.

An "aryl" refers to an optionally substituted aromatic group having at least one ring and includes carbocyclic and heterocyclic aryl structures. Examples of aryl substituents include alkyl, alkenyl, alkynyl, amino, substituted amino, amido, acetyl, substituted acetyl, carboxy, hydroxy, alkoxy, nitro, sulfonyl, halogen, optionally substituted phenyl and optionally substituted phenoxy; wherein the optionally substituted phenyl and optionally substituted phenoxy can have up to 5 subtituents each independently selected from the group consisting of alkyl, alkenyl, alkynyl, amino, substituted amino, amido, acetyl, substituted acetyl, carboxy, hydroxy, alkoxy, nitro, sulfonyl, and halogen.

An "aryloxy" refers to a "—O-aryl" where the "aryl" is defined as described above and "O" is an oxygen. Preferably, the aryloxy is phenoxy.

A "carbocyclic" refers to a ring structure where all the atoms on the aromatic ring are carbon atoms. The carbon atoms are optionally substituted as described above for an aryl. Preferably, the carbocyclic aryl is an optionally substituted phenyl.

A "heterocyclic aryl" refers to an aryl having 1 or more, preferably 1 to 3, heteroatoms as ring atoms in the aromatic ring and the remainder of the ring atoms are carbon atoms. Suitable heteroatoms include oxygen, sulfur, and nitrogen. Examples of heterocyclic aryls include furanyl, thienyl, pyridyl, pyrrolyl, N-lower alkyl pyrrolo, pyrimidyl, pyrazinyl, and imidazolyl. The heterocyclic aryl is optionally substituted as described above for an aryl.

"Nitro" refers to $NO_2$.

A "substituted acetyl" refers to $C(=O)-CH(R)_2$, where each R is a non-reactive chemical atom or atoms, provided that at least one R is not hydrogen. Examples of R include hydrogen, lower alkyl, lower alkenyl, lower alkynyl, phenyl, amino, carboxy, and alkoxy.

A "substituted amino" refers to $-NH-R$ where R is a non-reactive chemical atom or atoms. Examples of R include lower alkyl, lower alkenyl, lower alkynyl, phenyl, amino, carboxy, and alkoxy.

A "substituted phosphorous" refers to $-P(R)_3$ where each R is a non-reactive chemical atom or atoms. Examples of R include O, =O, S, $CH_3$ and alkoxy.

A "substituted sulfur" refers to the presence of an atom or atoms, other than hydrogen, which obey chemical stoichiometry and is non-reactive.

"Sulfonyl" refers to $S(O)_2-R$, where R is a non-reactive atom or atoms. Examples of R include lower alkenyl, lower alkynyl, phenyl, halogen, amino, and substituted amino.

More preferably, the chemiluminescent label is made up of an optionally substituted acridinium joined to a leaving group as illustrated in Structure IV.

Structure IV

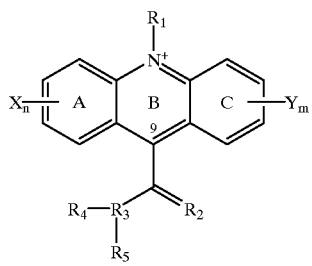

where
R₁ is selected from the group consisting of H, alkyl, alkenyl, alkynyl, and aryl; preferably R₁ is a lower alkyl, more preferably methyl;
n is either 0, 1, 2, 3, or 4; preferably n is either 0, 1 or 2;
m is either 0, 1, 2, 3, or 4; preferably m is either 0, 1, or 2;
each X is independently selected from the group consisting of alkyl, alkenyl, alkynyl, amino, substituted amino, carboxy, hydroxy, alkoxy, nitro, sulfonyl, halogen, thiol, amido, acetyl, substituted acetyl, optionally substituted phenyl and optionally substituted phenoxy; wherein the optionally substituted phenyl and optionally substituted phenoxy can have up to 5 substituents each independently selected from the group consisting of alkyl, alkenyl, alkynyl, amino, substituted amino, amido, acetyl, substituted acetyl, carboxy, hydroxy, alkoxy, nitro, sulfonyl, and halogen. In different embodiments each X is independently an alkyl or an alkoxy, each X is independently a lower alkyl or a lower alkoxy, and each X is independently methyl or methoxy;
each Y is independently selected from the group consisting of alkyl, alkenyl, alkynyl, amino, substituted amino, carboxy, hydroxy, alkoxy, nitro, sulfonyl, halogen, thiol, amido, acetyl, substituted acetyl, optional substituted phenyl and optionally substituted phenoxy; wherein the optionally substituted phenyl and optionally substituted phenoxy can have up to 5 substituents each independently selected from the group consisting of alkyl, alkenyl, alkynyl, amino, substituted amino, amido, acetyl, substituted acetyl, carboxy, hydroxy, alkoxy, nitro, sulfonyl, and halogen. In different embodiments each Y is independently an alkyl or an alkoxy, each Y is independently a lower alkyl or a lower alkoxy, and each Y is independently methyl or methoxy; and
$R_2$, $R_3$, $R_4$ and $R_5$ are defined as described above for a Structure III molecule.

Additional embodiments provide for chemiluminescent molecules joined to leaving groups having a heterocyclic ring system selected from the group consisting of: benz[a]acridinium, benz[b]acridinium, benz[c]acridinium, benzimidazole cation, quinolinium, isoquinolinium, quinolizinium, cyclic substituted quinolinium, pyridinium, pyrimidininium, pyridazinium, pyrazininium, phenathridinium and quinozalinium; where each ring of the ring system is substituted in the same manner as a Structure IV molecule such that each available carbon can each independently have a X/Y substituent, more preferably each ring contains 0 to 2 substituents and one of the rings is a positively charged heterocyclic ring containing a N joined to R₁ and a carbon atom joined to a linking group; and where the molecule can be protected from chemical or enzymatic alteration by a protection probe.

EXAMPLES

Examples are provided below illustrating different aspects and embodiments of the present invention. The examples include techniques that can be used to determine the suitability of different labels, protection probes and detection probes. These examples are not intended to limit the claimed invention.

Transcription-Based Amplification Conditions

With the exception of varying target concentration, standard transcription-based amplification reactions contained 30 pmol/reaction of the specified T7 promoter-primer, 30 pmol/reaction of the specified primer, 35 mM KCl, 75 mM Tris-Cl pH 7.5, 9 mM HEPES pH 7.5, 20 mM $MgCl_2$, 1 mM dATP, 1 mM dCTP, 1 mM dGTP, 1 mM dTTP, 4 mM ATP, 4 mM CTP, 4 mM GTP, 4 mM UTP, 5% w/v PVP, 10% v/v glycerol, 12.5 mM NALC, 0.75 mM EDTA, 2.5% Triton®X-102 (Sigma), 0.0025% phenol red, 100–200 Epicentre units of reverse transcriptase (Epicentre Technologies Inc.) and about 500 Epicentre units of T7 RNA polymerase (Epicentre Technologies Inc.) in a 100 μl reaction volume, unless otherwise noted.

Probe-in-Amp transcription-based amplification conditions were the same as above, with the addition of approximately 0.1 pmol of the specified acridinium ester (AE) labeled probe, which was added to the transcription-based amplification reaction with the enzyme reagent. When protection probes were used, the AE-labeled probe was hybridized to the stated amount of the indicated protection probe prior to addition to the transcription-based amplification reaction with the enzyme reagent.

For 100 μl amplification reactions, 25 μl of amplification reagent was aliquoted to individual tubes, followed by the addition of 200 μl of mineral oil. Target RNA (rRNA isolated from target organisms) was diluted to the appropriate copy number in water and added in a 50 μl volume. Reactions were incubated at 95° C. (in a water bath) for 10 minutes, then transferred to 42° C. for 5 minutes. Enzyme reagent (25 μl) containing reverse transcriptase and T7 RNA polymerase, with or without labeled detection probe or protection probe, was then added and then reaction tubes were incubated at 42° C. for an additional 60–120 minutes. Reactions were terminated by the addition of Hybridization Buffer (0.05 M lithium succinate pH 5, 0.6 M lithium chloride, 1% w/v lithium lauryl sulfate (LLS), 10 mM EDTA, and 10 mM EGTA), which was the initial step in the amplicon detection method.

HPA Detection

Amplicon production was detected by hybridization with AE-labeled oligonucleotide detection probes (e.g. see Arnold et al., U.S. Pat. No. 5,283,174 hereby incorporated by reference herein), either added after the amplification reaction, or included with the amplification enzyme reagent (Probe-in-Amp). In some instances one or more unlabeled helper oligonucleotides were used to facilitate hybridization to the nucleic acid having the target sequence. (See Hogan et. al., U.S. Pat. No. 5,030,557.)

Hybridization of the labeled detection probes added after the transcription-based amplification reaction or for Probe-in-Amp was performed in a solution containing Hybridization Buffer at 60° C. for 10 minutes. Hybridization Buffer was normally made as a 2× stock containing labeled detection probe and an equal volume was added to each amplification reaction. The same hybridization reagent without probe was added to Probe-in-Amp reactions that included AE-labeled probe with or without protection probe, then hybridization was conducted as above. Following the 10 minute hybridization at 60° C., 300 µl (3× reaction volume) of selection reagent containing 0.15 M sodium tetraborate pH 8.5, and 1% Triton®X-100 was added to each tube and the reactions were incubated at 60° C. for an additional 15 minutes.

Detection and quantitation of hybridization complexes were accomplished using a luminometer. The luminometer automatically injects two reagents, the first being composed of 1 mM nitric acid and 0.1% hydrogen peroxide (v/v), the second being 1 N sodium hydroxide. The reagents cause the formation of chemiluminescence from unaltered acridinium esters present in AE-labeled oligonucleotides. Assay results were given in Relative Light Units (RLUs), a relative measure of the number of photons detected by the luminometer.

Nucleic Acid Sequences

SEQ. ID. No. 1: GGA GGA UAU GUC UCA GCG CUA CC
SEQ. ID. No. 2: GGA GGA TAT GTC TCA GCG CTA CC
SEQ. ID. No. 3: AAT TTA ATA CGA CTC ACT ATA GGG AGA CCA GGC CAC TTC CGC TAA CC
SEQ. ID. No. 4: CGC GGA ACA GGC TAA ACC GCA CGC
SEQ. ID. No. 5: CGG CTG AGA GGC AGT ACA GAA AGT GTC GTG GTT AGC GG
SEQ. ID. No. 6: GGG TAA CCG GGT AGG GGT TGT GTG TGC GGG GTT GTG
SEQ. ID. No. 7: ATG CGT CTT GAG G
SEQ. ID. No. 8: TGC GTC TTG AG
SEQ. ID. No. 9: GGA CCU CAA GAC GCA UGU C
SEQ. ID. No. 10: GAA ATT AAT ACG ACT CAC TAT AGG GAG ACC ACA GCC GTC ACC CCA CCA ACA AGC T
SEQ. ID. No. 11: GGG ATA AGC CTG GGA AAC TGG GTC TAA TAC C
SEQ. ID. No. 12: GTC TTG TGG TGG AAA GCG CTT TAG
SEQ. ID. No. 13: CTA AAG CGC TTT CCA CCA CAA GAC ATG CAT CCC GTG GTC CTA TCC GG
SEQ. ID. No. 14: GCT TTC CAC CAC AAG AC
SEQ. ID. No. 15: AGA GTC CGT AGA GCG ATG AGA ACG
SEQ. ID. No. 16: CAT CGC TCT ACG GAC
SEQ. ID. No. 17: CGC TCT ACG GAC TC
SEQ. ID. No. 18: CGT TCT CAT CGC TCT ACG GAC TCT

Oligonucleotides of SEQ. ID. Nos. 1, 2, 9, 12, and 15 contained an AE label. AE-labeled probes SEQ. ID. Nos. 1 and 2, as well as protection probe SEQ. ID. Nos. 7, 8, and 14 used in the examples below, were blocked at the terminal 3' OH by an n-propyl group.

Example 1

AE-Labeled Probe Is Stable In Transcription-Based Amplification Conditions

Approximately 0.1 pmol of an AE-labeled probe with either an RNA backbone, SEQ. ID. No. 1, or DNA backbone, SEQ. ID. No. 2, was incubated for up to 60 minutes in standard transcription-based amplification conditions at 42° C. (except that T7 RNA polymerase was excluded from the mixture so that amplification could not take place). Amplification primers SEQ. ID. Nos. 3 and 4 were included in each reaction, but no target RNA was added.

Aliquots of the transcription-based amplification mixture containing the probe were withdrawn at various time points and detected directly in a luminometer to determine the amount of RLU remaining compared to the input RLU, and thus estimate the stability of the AE-labeled probe. The result of this experiment (data not shown) was that there was about a 10% decrease in RLU after one hour.

Example 2

Probe-In-Amp Vs. Transcription-Based Amplification Without Probe

This example compares normal transcription-based amplification detected by adding and hybridizing the AE-labeled probe after completion of the amplification reaction with a Probe-in-Amp amplification. The Probe-in-Amp amplification contained an AE-labeled probe added with the enzyme reagent and, thus, the AE-labeled probe was present during the amplification reaction.

In this example, transcription-based amplification conditions were similar to the standard conditions described above, except the final volume was 50 µl, 15 pmol of each primer (SEQ. ID. Nos. 3 and 4) was used instead of 30 pmol, and the amplification included 0.02% BSA.

Amplification reactions (6 replicates each) were prepared with 0, 5 fg or 25 fg of *M. tuberculosis* rRNA target (0, 2000, or 10,000 copies). In Probe-in-Amp reactions, 0.1 pmol of RNA probe SEQ. ID. No. 1 was added to the reaction mixture along with the enzyme reagent, and thus was present during the amplification.

After amplification, 10 µl of each normal or Probe-in-Amp reaction was diluted to 100 µl with water, and detected by HPA as described above. Amplicon in the Probe-in-Amp reactions was detected using only labeled detection probe added before amplification. Amplicon in normal amplification reactions was detected by addition of 0.1 pmol of RNA probe SEQ. ID. No. 1 or DNA probe SEQ. ID. No. 2 plus 2.5 pmol of DNA helper probes SEQ. ID. Nos. 5 and 6 following the protocol described above.

Results in Table 1 show that significant amplification and detection occurs in the Probe-in-Amp (PiA) amplification reactions, but the signal is about 5–10% of the normal amplification reaction followed by separate HPA detection.

TABLE 1

| Target input | RNA PiA | RNA HPA | DNA HPA + helpers |
|---|---|---|---|
| 0 fg | 5968 | 1349 | 1612 |
| 5 fg | 39632 | 703160 | 777808 |
| 25 fg | 126595 | 914840 | 1101539 |

The RNA probe also produces a higher background signal in the Probe-in-Amp reaction than normal amplification and HPA. RNA probe alone and DNA probe plus helper probes yield similar RLU values in normal amplification/HPA reactions, indicating that the lower signals from Probe-in-Amp reactions were due to decreased amplification efficiency, or loss of probe during amplification.

Example 3

Design and Selection of A Protection Probe for an AE-Labeled Probe

This example illustrates the use of different factors for designing a protection probe for use with an AE label. Such factors can be applied to other types of labels.

Protection probes were designed to remain hybridized to the AE-labeled probe until hybridization of the probe to its target, usually at 60° C. The function of the protection probe is to stabilize the AE label to as high a temperature as required, but to avoid interfering with hybridization to target and producing high background signals during HPA.

A protection probe is preferably designed to be shorter than the AE-labeled probe it will protect to help ensure that the AE-labeled probe will hybridize to its target more readily than the protection probe during HPA. The protection probe is preferably balanced in its calculated Tm and G:C content both 5' and 3' from the AE label. The overall Tm of the protection probe to the detection probe will be high enough to provide the required stability, but low enough not to interfere during HPA of the probe with its target. In addition, if the protection probe is to be used for Probe-in-Amp, the 3' end is preferably blocked so that it can not be extended by reverse transcriptase while hybridized to the AE-labeled probe. The protection probe is usually present in a molar excess to the AE-labeled probe to ensure stable hybridization.

Several assays can be performed to characterize protection probes for a specific AE-labeled detection probe. The first is to determine the molar excess of protection probe to AE-labeled probe that gives maximum protection to the probe. This can be done, for example, by HPA of various ratios of the detection probe:protection probe hybridization complex at a temperature below the calculated Tm (as described above).

Table 2 illustrates the results from a quantitative HPA assay performed as described above at 42° C. on the AE-labeled probe SEQ. ID. No. 12 with protection probe SEQ. ID. No. 14 (acting as target in this assay). The amount of protection probe SEQ. ID. No. 14 ranged in concentration from none to 100-fold molar excess over the AE-labeled probe.

TABLE 2

| Fold PPO concentration | RLU |
| --- | --- |
| 0 | 271 |
| 0.5 | 94231 |
| 1 | 193918 |
| 2 | 249342 |
| 5 | 246774 |
| 10 | 248502 |
| 50 | 255087 |
| 100 | 258335 |

Table 2 comparing the molar excess of protection probe versus the RLU shows that signals were saturated at 2-fold excess protection probe, indicating that this concentration produced nearly maximum protection under these conditions. Good protection probes are preferred at low concentrations for maximum stabilizing effect; 2 fold excess is considered very good.

Next, the stability of the label in the detection probe:protection probe hybridization complex should be estimated and compared between protection probe candidates. The stability of the label in the hybridization complex can be estimated by determining the time at which RLU reaches half of the input RLU during the selection step of HPA performed at a temperature lower than the estimated Tm. Conditions are chosen such that the protection probe is in molar excess over AE-labeled probe, and the amount of AE-labeled probe will produce RLU within the linear range of the luminometer.

The AE-labeled probe is hybridized to excess protection probe in hybridization buffer as described above, then selection reagent is added and incubated at the same temperature. Aliquots are removed at time points and the log of the percent of the remaining RLU is plotted versus time. The point at which a line plotted through the linear range of points passes through log(50%) is called the $T_{1/2}$ of hydrolysis of the label. A larger value for $T_{1/2}$ of hydrolysis indicates a more stable label in the detection probe:protection probe hybridization complex.

FIG. 1 provides an example of determining $T_{1/2}$ of the hydrolysis of the label. AE-labeled probe SEQ. ID. No. 12 (0.25 pmol) was used with 10-fold excess of protection probe SEQ. ID. No. 14 as the target. Hydrolysis was performed at 42° C., and aliquots removed and read in the luminometer at 0, 5, 10, 15, 30, and 45 minutes. "Control" refers to the same AE-labeled probe, but in the absence of protection probe (no target). $T_{1/2}$ of the control is the point at which a line plotted through the linear range passes through log(50%).

The FIG. 1 calculated $T_{1/2}$ of the hydrolysis of the label is about 54 minutes. Other shorter protection probes produced values for $T_{1/2}$ of the hydrolysis of the label of less than 5 minutes, so protection probe SEQ. ID. No. 14 was considerably more stable and thus was preferable.

After protection probes with acceptable concentrations and values for $T_{1/2}$ of the hydrolysis of the label are identified, the Tm of the protection probe to the AE-labeled probe should be determined. This is accomplished by forming the detection probe:protection probe hybridization complex, diluting and splitting into aliquots, incubating the aliquots at various temperatures to allow the detection probe:protection probe hybridization complex to denature at the melt temperature, then incubation with selection reagent at a temperature lower than the estimated Tm to hydrolyze unhybridized probe as described above. Aliquots are read in a luminometer, the percent of input RLU (100×RLU/input RLU) versus temperature is plotted for each point, and the temperature at which the RLU reaches 50% of the input RLU is called the Tm.

Figure 2:
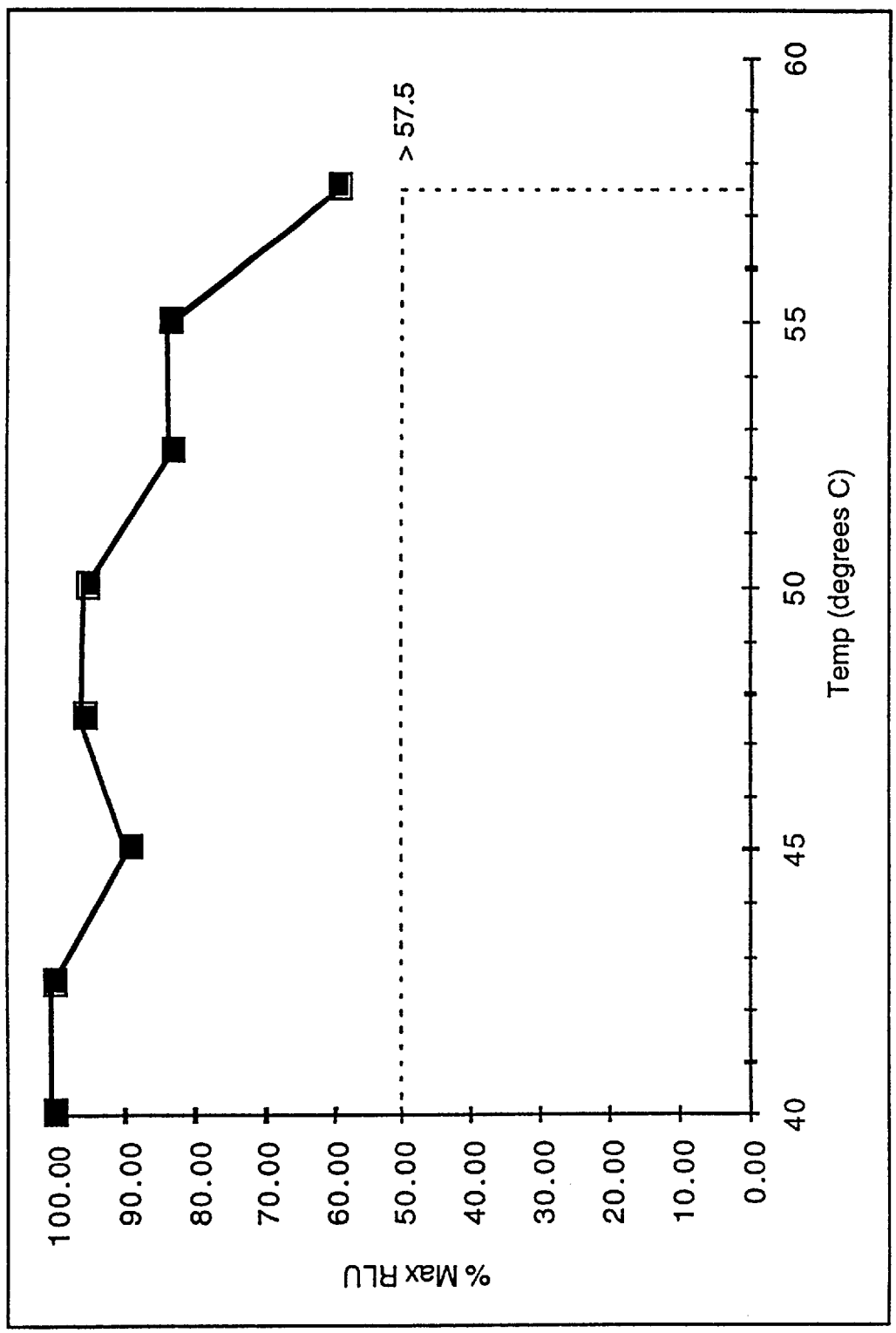
FIG. 2 illustrates the Tm determination of AE-labeled probe SEQ. ID. No. 12 with excess protection probe SEQ. ID. No. 14 as target. The percent input RLU was plotted versus temperature.

FIG. 2 illustrates the Tm determination of AE-labeled probe SEQ. ID. No. 12 (0.25 pmol) with 10-fold excess protection probe SEQ. ID. No. 14 as target. The procedure was performed in hybridization buffer using melt temperatures from 40° C. to 57.5° C. in 2.5° C. steps, and selecting at 42° C. FIG. 2 shows that the percent input RLU only approached 50% in this assay, so the Tm was higher than the highest temperature tested. An extrapolation can be made to estimate the Tm at about 58° C.

The high Tm estimated from FIG. 2 suggested a stable detection probe:protection probe hybridization complex and predicted good stability at higher temperatures. However, it should be confirmed that the protection probe does not interfere with normal HPA of the probe to its real target. To test this, AE-labeled probe SEQ. ID. No. 12 (0.01 pmol) was hybridized in Hybridization Buffer with protection probe SEQ. ID. No. 14 at a concentration range from equimolar to 100-fold excess. The detection probe:protection probe hybridization complex was then used in a normal HPA reaction at 60° C. as described above; negative reactions contained no added target and positive reactions contained excess oligonucleotide target of SEQ. ID. No. 13. An acceptable result would be that positive and negative HPA signals were about the same in the presence or absence of protection probe; especially that the negative reactions were not significantly increased due to the presence of protection probe.

Table 3 provides results showing that protection probe SEQ. ID. No. 14 did not interfere with positive or negative HPA for AE-labeled probe SEQ. ID. No. 12 in normal HPA conditions. Positive HPA signals were about the same in the presence or absence of protection probe, and negative HPA signals were not significantly increased with up to 100-fold excess of protection probe compared to no protection probe.

TABLE 3

| PPO conc./HPA | 0× | 1× | 2× | 5× | 10× | 50× | 100× |
|---|---|---|---|---|---|---|---|
| Negative | 362 | 352 | 351 | 371 | 398 | 430 | 401 |
| Positive | 91270 | 89089 | 91463 | 94903 | 94845 | 98583 | 93776 |

For optimal performance, it is very useful to design and choose a protection probe matched for its required function, as demonstrated in Tables 1–3 and FIGS. 1 and 2. Protection probe SEQ. ID. No. 14 performed well in these assays for AE-labeled probe SEQ. ID. No. 12, and would be expected to perform well in either Probe-in-Amp or stabilizing the probe for long term storage in liquid hybridization buffer.

Example 4

Efficiency of Probe-In-Amp Transcription-Based Amplification is Improved with Protection Probe A Probe-in-Amp experiment was done similar to Example 2, except that in some of the reactions, the AE-labeled probe included at the beginning of the amplification was prehybridized with a 5-fold or 10-fold excess of protection probe before being added to the amplification reaction. The employed protection probe was designed to remain hybridized to the AE-labeled probe during amplification. Hybridization of the detection probe to the protection probe prevents the detection probe from hybridizing to the amplicon during transcription-based amplification so it will not interfere with the reverse transcriptase extension reaction on the amplicon template.

The AE-labeled RNA probe SEQ. ID. No. 9 specific for *M. avium* rRNA amplicon generated with transcription-based amplification primers SEQ. ID. Nos. 10 and 11 was either a) added in Hybridization Buffer after amplification for a normal HPA detection; b) added by itself to the reaction mixture in the enzyme reagent prior to amplification; or c) prehybridized with a 5-fold or 10-fold excess of protection probe SEQ. ID. No. 7 or 8 for 30 minutes at 42° C. before to being added to the reaction mixture in the enzyme reagent prior to amplification. Hybridization and detection were performed for normal HPA or for Probe-in-Amp as described above. Results are shown in Table 4.

TABLE 4

| Target input | Normal HPA | 0× PPO | 5× PPO1 | 10× PPO1 | 5× PPO2 | 10× PPO2 |
|---|---|---|---|---|---|---|
| 0 fg | 7391 | 4149 | 4149 | 4149 | 4149 | 4149 |
| 25 fg | 264489 | 26958 | 68639 | 357306 | 523427 | 424783 |
| 250 fg | 1290650 | 626945 | 611522 | 522248 | 601930 | 605679 |

"PPO1" refers to SEQ. ID. No. 8 and "PPO2" refers to SEQ. ID. No. 7. "Target input" refers to amount of *M. avium* rRNA amplified.

The effectiveness of the protection probe in decreasing inhibition of Probe-in-Amp amplification is apparent especially when pre-hybridized to the probe in 10-fold excess amplified at the 25 fg target level. Signal from Probe-in-Amp without protection probe was about 27,000 RLU, but when the AE-labeled probe was protected with protection probe 1 or protection probe 2, signals rose to about 350,000 to about 500,000 RLU, a 20-fold increase in amplification efficiency. Signals at 250 fg of rRNA target were not much higher, probably because the probe was reaching saturation with amplicon. Normal HPA signals are shown for comparison.

Example 5

Protection Probe Extends Stability of AE-Labeled Probe During Storage in Solution AE-labeled probes hybridized to complementary protection probes are more stable during storage in solution. This example illustrates the increased stability in long term storage of labeled detection probes with the labeled probe/protection probe combination characterized and predicted to be acceptable in Example 3.

AE-labeled probe SEQ. ID. No. 12 (0.01 pmol) was prehybridized to a two-fold excess of protection probe SEQ. ID. No. 14 at 42° C. for 30 minutes and stored in 2× Hybridization Buffer at 4° C. and 25° C. for up to 6 months. Stability of labeled probe hybridized to protection probe was compared to probe without labeled probe stored in 2× Hybridization Buffer at −20° C., 4° C. and 25° C.

Figure 3:
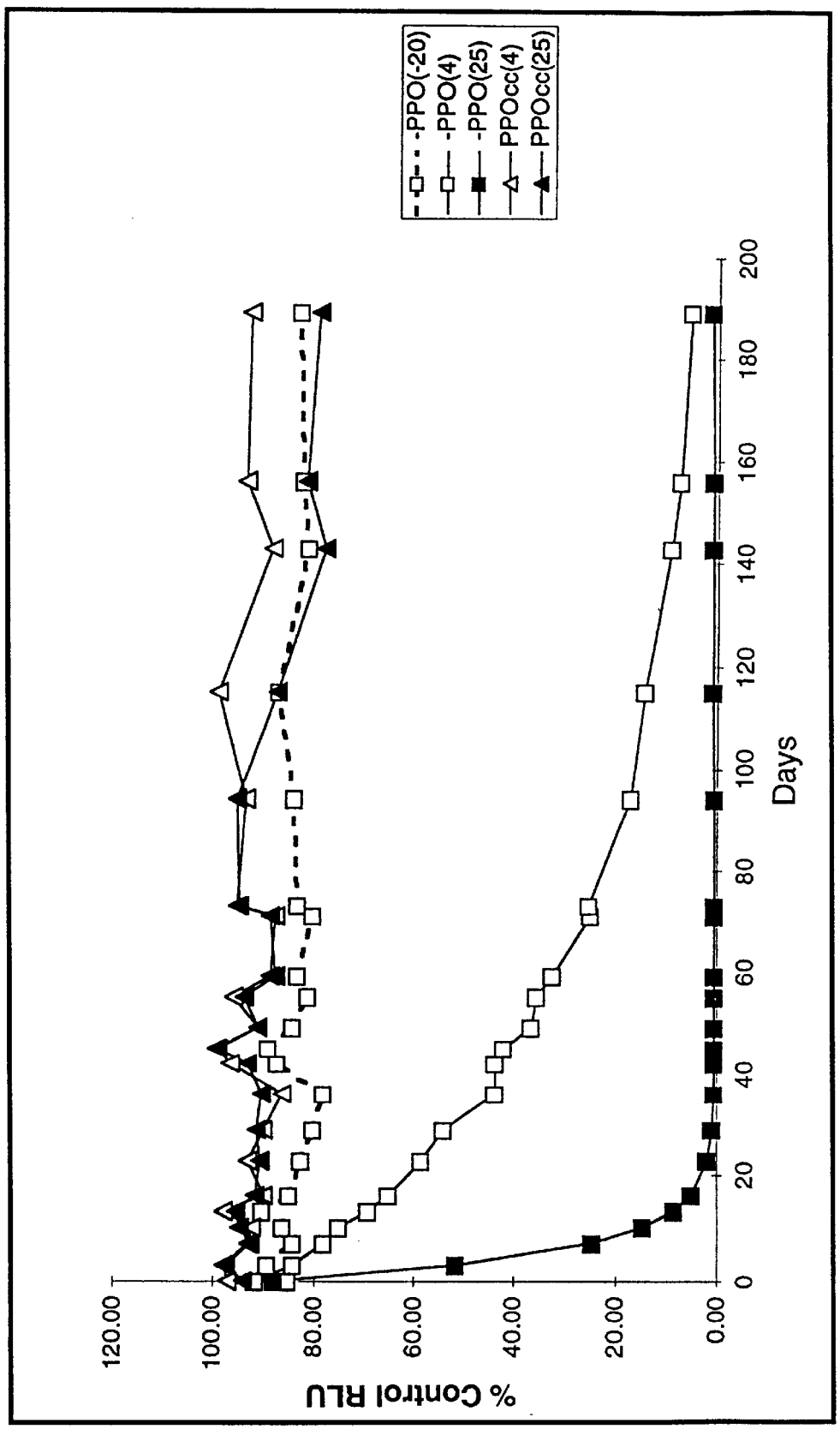
FIG. 3 illustrates the ability of protection probes to affect the stability of labeled probes during storage at different temperatures. The temperatures provided in parenthesis are in ° C. "-PPO" refers to labeled probe in the absence of a protection probe. "PPOcc" refers to the presence of protection and detection probes.

Aliquots were withdrawn at various time points, and the stability of the labeled probe was quantitatively determined by HPA with excess complementary target (SEQ. ID. No. 13). The amount of RLU remaining was plotted as the percentage of RLU remaining compared to the initial signal on day 0. Two different aliquots of probe from each storage condition were maintained, and 3 replicates for each were assayed by HPA at each time point (RLUs from the 6 replicates for each condition were averaged). Results for the 6 month stability study are shown in FIG. 3.

A dramatic increase in stability in the AE-labeled probe is apparent by comparing time points of AE-labeled probe alone versus AE-labeled probe hybridized to protection probe. The AE-labeled probe was relatively stable at −20° C. without protection probe. However, at 4° C., labeled probe without protection probe degraded to 80% of original signal after about 1 week, while with protection probe, the same AE-labeled probe retained greater than 80% of its original RLU after 6 months. In addition, when hybridized to the protection probe, the AE-labeled probe retained greater than 80% of its original RLU at 6 months even at 25° C. Without protection probe, the probe lost 50% of its original signal within 3 days (the first time point) at 25° C.

Example 6

Stability of AE-Labeled Probe with Two Different Protection Probes

This example presents an experiment similar to Example 5, but with a different AE-labeled probe, and compares stability in solution when hybridized to one of two complementary protection probes. AE-labeled probe SEQ. ID. No. 15 (0.01 pmol) was prehybridized to a 20-fold excess of protection probe SEQ. ID. No. 16 (PPOa in FIG. 4) or a 10-fold excess of protection probe SEQ. ID. No. 17 (PPOc in FIG. 4) at 50° C. for 8 minutes, followed by a hybridization at 42° C. for 8 minutes and storage in 2× Hybridization Buffer at 4° C. and 25° C. for up to 6 months.

Figure 4:
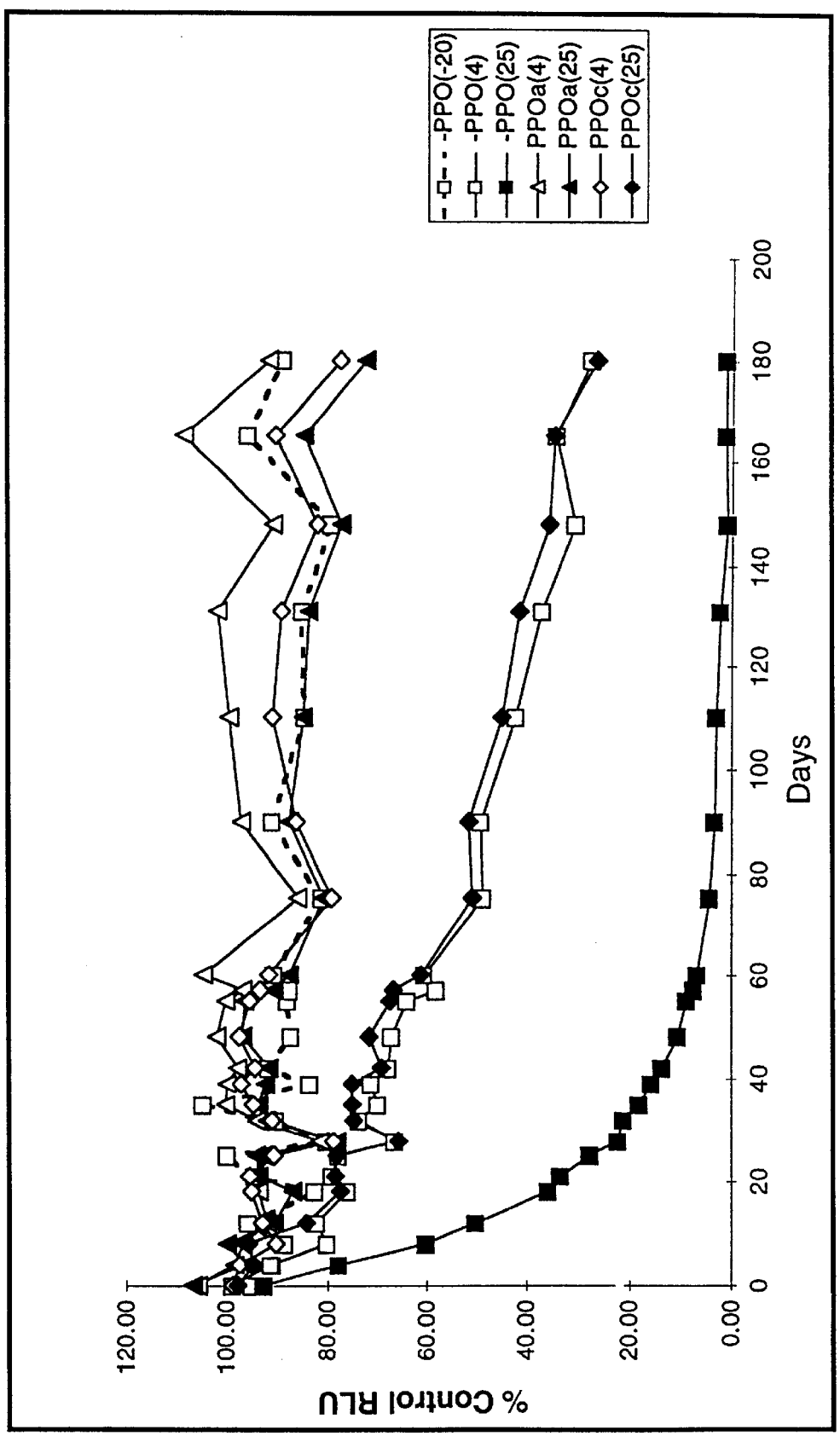
FIG. 4 illustrates the ability of different protection probes to affect the stability of labeled probes during storage at different temperatures. The temperatures provided in parenthesis are in ° C. "-PPO" refers to labeled probe in the absence of a protection probe. "PPOa" refers to the presence of a labeled probe and a protection probe of SEQ. ID. No. 16. "PPOc" refers to the presence of a labeled probe and a protection probe of SEQ. ID. No. 17.

Stability of labeled probe hybridized to protection probes was compared to labeled probe without protection probe stored in 2× Hybridization Buffer at −20° C., 4° C. and 25° C. Aliquots were withdrawn at various time points, and the stability of the probe was quantitatively determined by HPA with excess complementary target (SEQ. ID. No. 18). The amount of RLU remaining was plotted as the percentage of RLU remaining compared to the initial signal on day 0. Two different probe aliquots from each storage condition were maintained, and 3 replicates for each were assayed by HPA at each time point (RLUs from the 6 replicates for each condition were averaged). Results for the 6 month stability study are shown in FIG. 4.

AE-labeled probe hybridized with protection probe was much more stable during storage than labeled probe without protection probe. Labeled probe with protection probe ("PPOa" in FIG. 4) retained greater than 80% of its original signal after 6 months at 4° C. or 25° C. Labeled probe with protection probe ("PPOc" in FIG. 4) retained greater than 80% of its original signal after six months at 4° C., but dropped below 80% at 25° C. after about 3 weeks. These results are compared to labeled probe without protection probe, which lost 80% of original signal after less than a week at 25° C. and after about three weeks at 4° C.

In this study, protection probe "a" stabilized the AE-labeled probe significantly better than protection probe "c"; and the labeled probe was about as stable at 25° C. with protection probe "a" as with protection probe "c" at 4° C. This was probably because protection probe "a" is longer and had a higher Tm when hybridized to detection probe, than protection probe "c".

Other embodiments are within the following claims. Thus, while several embodiments have been shown and described, various modifications may be made without departing from the spirit and scope of the present invention.

What is claimed is:

1. A composition comprising:

a detection probe comprising a label susceptible to a chemical or enzymatic alteration, and a protection probe that protects said label from said alteration, provided that a hybridization complex formed between said detection probe and said protection probe has a lower Tm than a hybridization complex formed between said detection probe and a fully complementary target nucleic acid.

2. The composition of claim 1 further comprising an aqueous solution, wherein said label is susceptible to said alteration in said solution and said alteration causes a loss of signal detectability from said label.

3. The composition of claim 2, wherein said hybridization complex formed between said detection probe and said protection probe has a Tm at least about 4° C. lower in a solution containing 0.05 M lithium succinate, pH 5.0, 0.6 M LiCl, 1% w/v LLS, 10 mM EDTA, and 10 mM EGTA, than said hybridization complex formed between said detection probe and said fully complementary target nucleic acid.

4. The composition of claim 3, wherein said hybridization complex formed between said detection probe and said protection probe has a Tm at least 5° C. lower in said solution than said hybridization complex formed between said detection probe and said fully complementary target nucleic acid.

5. The composition of claim 2, wherein said label can be hydrolyzed in a solution at 37° C. consisting of 0.05 M lithium succinate, pH 5.0, 0.6 M LiCl, 1% w/v LLS, 10 mM EDTA, and 10 mM EGTA, and said protection probe protects said label from hydrolysis.

6. The composition of claim 1, wherein said label is a luminescent label.

7. The composition of claim 6, wherein said label is a chemiluminescent label.

8. The composition of claim 7, wherein chemiluminescence from said label proceeds via an electronically excited optionally substituted N-alkyl acridone.

9. The composition of claim 7, wherein said label comprises an optionally substituted acridinium ester.

10. The composition of claim 1, wherein said label comprises a labile ester linkage or a labile thioester linkage.

11. The composition of claim 1, wherein said detection probe is an optionally modified detection oligonucleotide, wherein each modification is independently selected from the group consisting of:

a 2'-modified ribose, a modified internucleotide linkage, a modified nitrogenous base, a peptide nucleic acid, and a 3' blocking group.

12. The composition of claim 11, wherein each modification to said optionally modified detection oligonucleotide is independently selected from the group consisting of:

2'-methoxy ribose, 2'-halo ribose, methylphosphonate linkage, phosphorothioate linkage, an alkyl blocking group, a 3'—3' inverted nucleotide, and a 3' deoxynucleoside.

13. The composition of claim 1, wherein said protection probe is an optionally modified protection oligonucleotide, wherein each modification is independently selected from the group consisting of:

a 2'-modified ribose, a modified internucleotide linkage, a modified nitrogenous base, a peptide nucleic acid, and a 3' blocking group.

14. The composition of claim 13, wherein each modification to said optionally modified protection oligonucleotide is independently selected from the group consisting of: 2'-methoxy ribose, 2'-halo ribose, methylphosphonate linkage, phosphorothioate linkage, an alkyl blocking group, a 3'—3' inverted nucleotide, and a 3' deoxynucleoside.

15. The composition of claim 13, wherein said protection probe is shorter than said detection probe.

16. The composition of claim 13, wherein said protection probe is not perfectly complementary to said detection probe.

17. The composition of claim 2, wherein said composition consists essentially of said protection probe, said detection probe, and said aqueous solution.

18. The composition of claim 17, wherein said composition consists of said protection probe, said detection probe, and said aqueous solution.

19. The composition of claim 1, wherein said protection probe is present in at least about a 2-fold excess to said detection probe.

20. The composition of claim 1, wherein said protection probe is present in at least a 4-fold excess to said detection probe.

21. The composition of claim 1, wherein said protection probe does not form a hydrolysis protecting adduct with said label.

22. A composition comprising:
an aqueous solution,
a detection means for detecting the presence of a nucleic acid sequence, wherein said detection means comprises a label susceptible to a chemical or enzymatic alteration in said aqueous solution,
a label protection means for inhibiting alteration of said label,
provided that a hybridization complex formed between said detection means and said label protection means has a lower Tm in said solution than a hybridization complex formed between said detection means and a fully complementary target nucleic acid of said detection means.

23. The composition of claim 22, wherein said hybridization complex formed between said detection means and said protection means has a Tm at least about 4° C. lower in a solution containing 0.05 M lithium succinate, pH 5.0, 0.6 M LiCl, 1% w/v LLS, 10 mM EDTA, and 10 mM EGTA, than said hybridization complex formed between said detection means and said fully complementary target nucleic acid.

24. The composition of claim 23, wherein said hybridization complex formed between said detection means and said protection means has a Tm at least 5° C. lower in said solution than said hybridization complex formed between said detection means and said fully complementary target nucleic acid.

25. The composition of claim 22, wherein said label can be hydrolyzed in said aqueous solution, and said protection means protects said label from hydrolysis.

26. The composition of claim 22, wherein said label is a luminescent label and said alteration causes a loss of signal detectability from said label.

27. The composition of claim 26, wherein said label is a chemiluminescent label.

28. The composition of claim 27, wherein chemiluminescence from said label proceeds via an electronically excited optionally substituted N-alkyl acridone.

29. The composition of claim 26, wherein said label comprises an optionally substituted acridinium ester.

30. The composition of claim 22, wherein said label comprises either a labile ester linkage or a labile thioester linkage.

31. The composition of claim 22, wherein said composition consists essentially of said protection means, said detection means, and said aqueous solution.

32. The composition of claim 31, wherein said composition consists of said protection means, said detection means, and said aqueous solution.

33. The composition of claim 22, wherein said protection means is present in at least about a 2-fold excess to said detection means.

34. The composition of claim 22, wherein said protection means is present in at least a 4-fold excess to said detection means.

35. The composition of claim 22, wherein said protection means does not form a hydrolysis protecting adduct with said label.

36. A composition consisting essentially of:
a detection means for detecting the presence of a target nucleic acid sequence,
an inhibiting means for inhibiting the ability of said detection means to hybridize to said target sequence during an isothermal amplification reaction, and
an optionally present aqueous solution,
provided that a hybridization complex formed between said detection means and said inhibiting means has a lower Tm than a hybridization complex formed between said detection means and fully complementary target nucleic acid of said detection means.

37. The composition of claim 36 wherein said inhibiting means does not form a hydrolysis protecting adduct with said detection means that decreases signal production from said detection means.

38. The composition of claim 37, wherein said aqueous solution is present, and said hybridization complex formed between said detection means and said inhibiting means has a Tm at least about 4° C. lower in said aqueous solution than said hybridization complex formed between said detection means and said fully complementary target nucleic acid.

39. The composition of claim 38, wherein said hybridization complex formed between said detection means and said inhibiting means has a Tm at least 5° C. lower in said solution than said hybridization complex formed between said detection means and said fully complementary target nucleic acid.

40. A method of determining whether a target nucleic acid sequence is present in a sample comprising the steps of:
a) producing a reaction mixture comprising said sample and a composition comprising a detection probe hybridized to a protection probe;
b) exposing said reaction mixture to amplifying conditions such that said target sequence, if present, is used to produce amplified nucleic acid, wherein under said amplifying conditions said detection probe is hybridized to said protection probe; and
c) detecting whether said detection probe is hybridized to said amplified nucleic acid under detection conditions as an indication that said target sequence is present in said sample, wherein under said detection conditions said detection probe is not stably hybridized to said protection probe and said detection probe hybridizes to said amplified nucleic acid if present.

41. The method of claim 40, wherein said amplifying conditions are transcription-based amplification conditions.

42. The method of claim 40, wherein under said detection conditions a detection probe:target nucleic acid Tm is at least about 5° C. greater than a detection probe:protection probe Tm.

43. The method of claim 42, wherein the temperature of said detection conditions is at least about 3° C. lower than said detection probe:target nucleic acid Tm, provided that said detection probe:protection probe Tm is at least about 2° C. lower than said temperature of said detection conditions.

44. The method of claim 43, wherein said detection probe:target nucleic acid Tm is at least 8° C. greater than said detection probe:protection probe Tm.

45. The method of claim 44, wherein the temperature of said detection conditions is at least 5° C. lower than said detection probe:target nucleic acid Tm.

46. The method of claim 40 wherein:
said detection probe comprises a label susceptible to a chemical or enzymatic alteration,
said alteration causes a loss of signal detectability from said label,
said protection probe corrects said label from said alteration in said steps (a) and (b), and
said protection probe does not form a hydrolysis protecting adduct with said label.

47. The method of claim 40, wherein:
said detection probe comprises a label susceptible to hydrolysis,
said hydrolysis causes a loss of signal detectability from said label,
said protection probe protects said label from said hydrolysis in said steps (a) and (b), and
said protection probe does not form a hydrolysis protecting adduct with said label.

48. The method of claim 46, wherein said label is a chemiluminescent molecule.

49. The method of claim 48, wherein said label comprises a labile ester linkage.

50. The method of claim 49, wherein chemiluminescence from said molecule proceeds via an electronically excited optionally substituted N-alkyl acridone.

51. The method of claim 49, wherein said label comprises an optionally substituted acridinium ester.

52. A method of determining whether a target nucleic acid sequence is present in a sample comprising the steps of:

a) producing a reaction mixture comprising a detection probe hybridized to a protection probe, provided that said detection probe comprises a label susceptible to a chemical or enzymatic alteration in said aqueous solution and said protection probe protects said label from said alteration, and b) providing said reaction mixture to said sample and detecting whether said detection probe is hybridized to said target sequence under detection conditions as an indication that said target sequence is present in said sample.

53. The method of claim 52, wherein said protection probe protects said label from hydrolysis in said reaction mixture prior to step b).

54. The method of claim 52, wherein a detection probe:target nucleic acid Tm is at least about 5° C. greater than a detection probe:protection probe Tm.

55. The method of claim 54, wherein the temperature of said detection conditions is at least about 3° C. lower than said detection probe:target nucleic acid Tm, provided that said detection probe:protection probe Tm is at least about 2° C. lower than said temperature of said detection conditions.

56. The method of claim 55, wherein said detection probe:target nucleic acid Tm is at least 8° C. greater than said detection probe:protection probe Tm.

57. The method of claim 56, wherein the temperature of said detection conditions is at least 5° C. lower than said detection probe:target nucleic acid Tm.

58. The method of claim 52, wherein said label is a chemiluminescent molecule and said alteration causes a loss of signal detectability from said label.

59. The method of claim 58, wherein said label comprises a labile ester linkage.

60. The method of claim 59, wherein chemiluminescence from said label proceeds via an electronically excited optionally substituted N-alkyl acridone.

61. The method of claim 59, wherein said label comprises an optionally substituted acridinium ester.

62. The method of claim 52, wherein said protection probe does not form a hydrolysis protecting adduct with said label.

* * * * *